United States Patent [19]

Corrigan et al.

[11] Patent Number: 4,987,767
[45] Date of Patent: Jan. 29, 1991

[54] EXPOSIVE DETECTION SCREENING SYSTEM

[75] Inventors: Colin D. Corrigan; Lawrence V. Haley; Douglas P. Menagh, all of Nepean, Canada

[73] Assignee: Research Corporation Technologies, Inc., Tucson, Ariz.

[21] Appl. No.: 447,724

[22] Filed: Dec. 8, 1989

Related U.S. Application Data

[63] Continuation-in-part of Ser. No. 364,663, Jun. 9, 1989, abandoned.

[51] Int. Cl.$^5$ .......................................... G01N 30/00
[52] U.S. Cl. ............................... 73/23.36; 73/23.37; 73/38.04; 73/864; 73/28.01; 73/864; 340/632
[58] Field of Search ............... 73/23.1, 23, 28, 864.73, 73/864, 863.81; 250/288; 340/632, 945

[56] References Cited

U.S. PATENT DOCUMENTS

| | | |
|---|---|---|
| 3,410,663 | 11/1968 | Reilly et al. |
| 3,430,482 | 3/1969 | Dravnieks et al. ........... 73/23.1 |
| 3,461,727 | 8/1969 | Everhard et al. |
| 3,725,895 | 4/1973 | Haynes ........................ 73/23 |
| 3,768,302 | 10/1973 | Barringer |
| 3,920,987 | 11/1975 | Anbar et al. |
| 3,925,022 | 12/1975 | Showalter et al. |
| 3,942,357 | 3/1976 | Jenkins ........................ 73/23 |
| 3,997,297 | 12/1976 | Jenkins et al. |
| 3,997,787 | 12/1976 | Fearon et al. |
| 3,998,101 | 12/1976 | Bradshaw et al. |
| 4,045,997 | 9/1977 | Showalter et al. ........... 340/632 X |
| 4,056,969 | 11/1977 | Barringer |
| 4,069,018 | 1/1978 | Karna et al. |
| 4,111,049 | 9/1978 | Lerner et al. |
| 4,127,395 | 11/1978 | McKey et al. |
| 4,202,200 | 5/1980 | Ellson |
| 4,580,440 | 4/1986 | Reid et al. |
| 4,718,268 | 1/1988 | Reid et al. |
| 4,775,484 | 10/1988 | Schmidt et al. |
| 4,818,870 | 4/1989 | Griffiths ........................ 73/864.73 X |
| 4,819,477 | 4/1989 | Fisher et al. ................... 73/28 X |
| 4,820,920 | 4/1989 | Bather ........................... 250/288 X |

FOREIGN PATENT DOCUMENTS 8800590 10/1988 World Int. Prop. O.

OTHER PUBLICATIONS

Romine Deming, "High Speed Detection of Plastic Explosives", May 14-16, 1986.
Martin J. Cohen, et al., "The Ion Mobility Spectrometer for High Explosive Vapor Detection."
Glenn E. Spangler, et al., "Recent Advances in Ion Mobility Spectrometry for Explosive Vapor Detection".
Roger F. Wernlund, et al., "The Ion Mobility Spectrometer As An Explosive or Taggant Vapor Detector".
M. W. Siegel, "Atmospheric Pressure Ionization Mass Spectrometry for Explosives Detection and Identification".

(List continued on next page.)

Primary Examiner—Hezron E. Williams
Assistant Examiner—Joseph W. Roskos
Attorney, Agent, or Firm—Scully, Scott, Murphy & Presser

[57] ABSTRACT

An explosive detection screening system used for the detection of explosives and other controlled substances such as drugs or narcotics. The screening system detects the vapor and/or particulate emissions from the aforementioned substances and reports that they are present on an individual or object and the concentration of each substance detected. The screening system comprises a sampling chamber for the collection of the vapor and/or particulate emissions, a concentration and analyzing system for the purification of the collected vapor and/or particulate emissions and subsequent detailed chemical analysis of the emissions, and a control and data processing system for the control of the overall system.

73 Claims, 14 Drawing Sheets

OTHER PUBLICATIONS

Lorne Elias, "Recent Projects at NRC Related to Explosives Detection".
P. J. Thoma, "Explosives Vapor Preconcentrator".
Frank J. Conrad, "Explosives Detection Program at Sandia National Laboratories".
Ralph L. Schellenbaum, "Air Flow Studies for Personnel Explosives Screening Portals".
James H. Henry, "A Review of Technology for Detection of Explosives" SPIE vol. 108 (1977).
G. Seman et al., "Detection of Hidden Explosives on Passenger Aircraft Using Hand Searchers, Biosensors, and Vapor Detectors".
William A. Wall, et al., "Determination of the Sensitivity and Specificity of Vapor Detection Systems for Explosives, Narcotics and Related Compound".
Anthony Jenkins, et al., "Improved Efficiency Access Control Equipment and Explosive, Weapons and Drug Abuse Detection".
Lawrence W. Hruboch, et al., "Study of Conventional Preconcentration Techniques for Explosive Vapors".

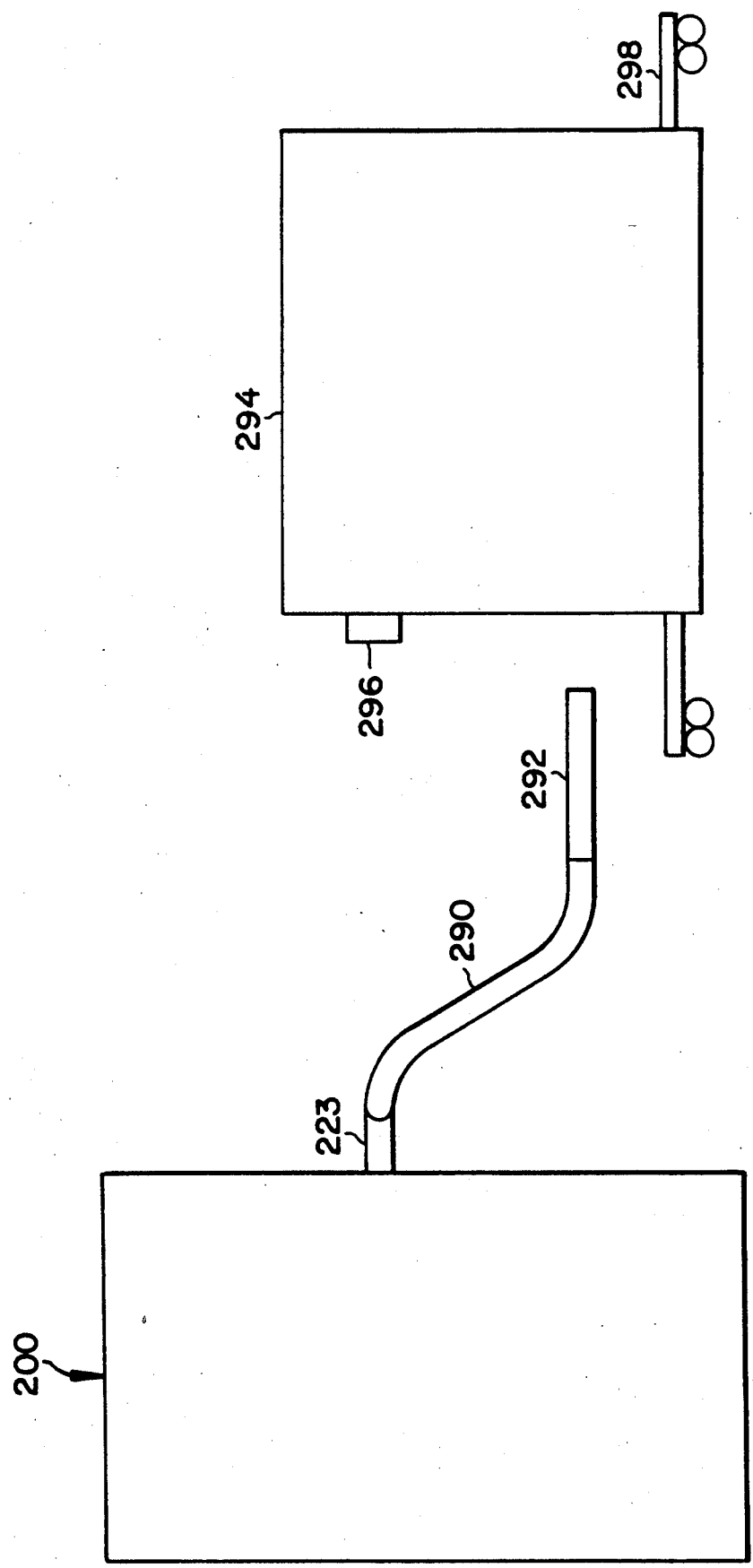

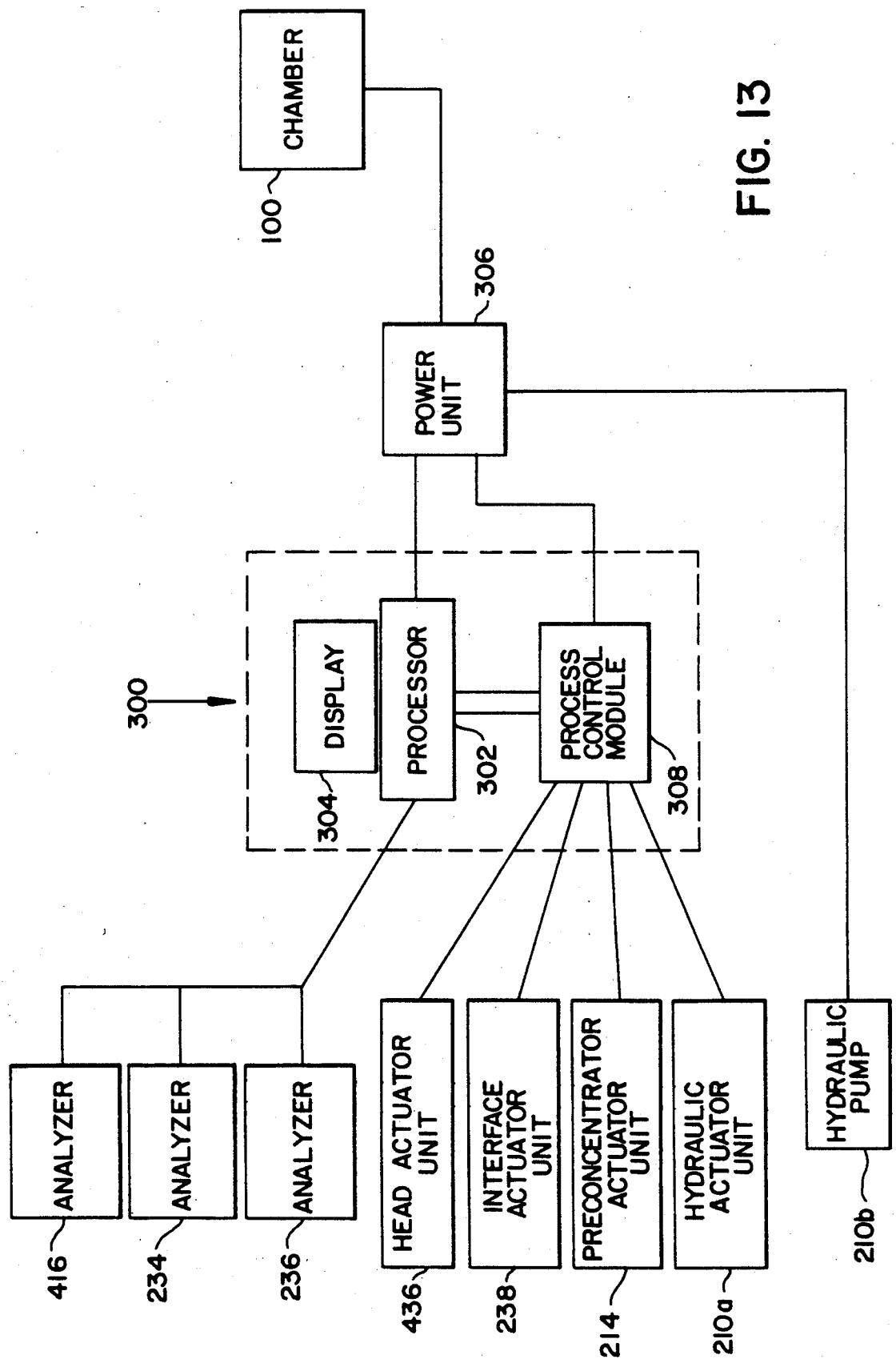

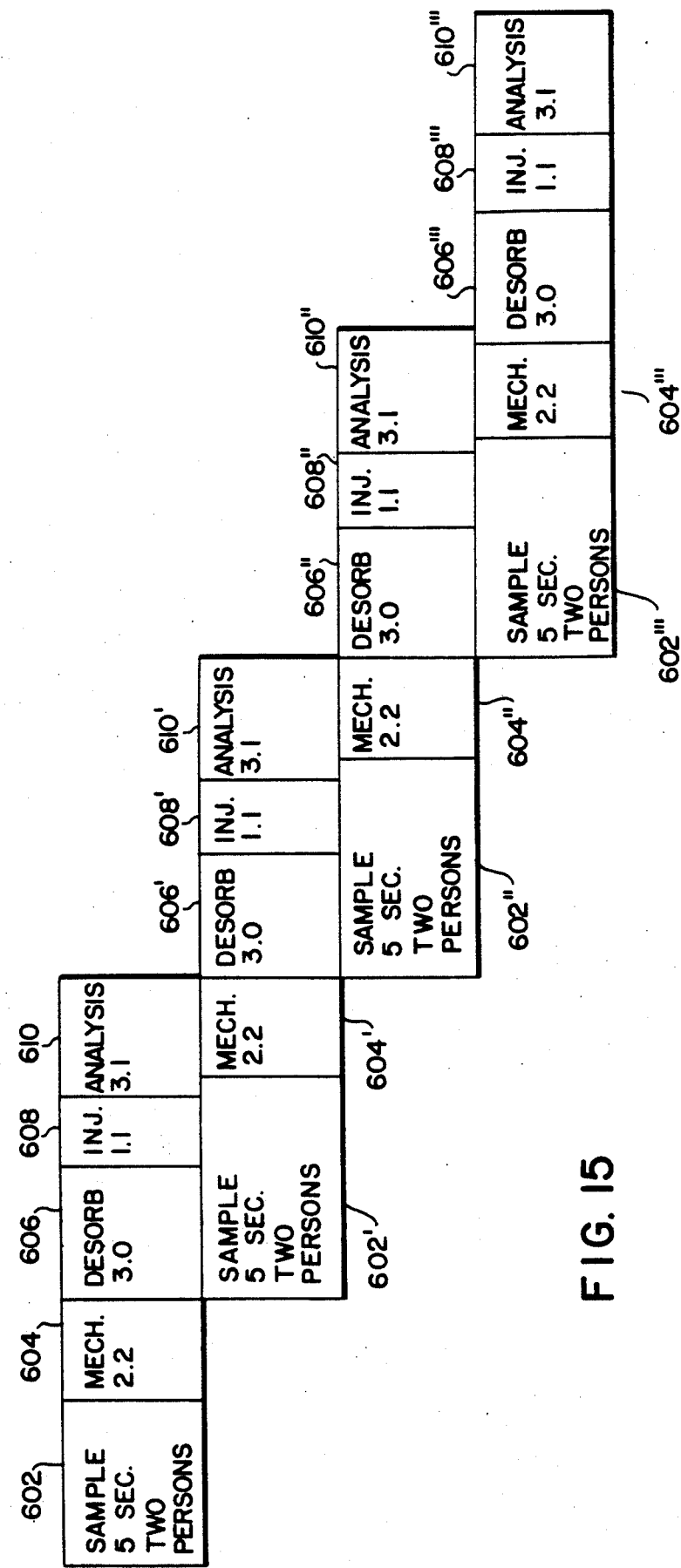

EXPOSIVE DETECTION SCREENING SYSTEM

This application is a continuation-in-part, of application Ser. No. 364,663, filed June 9, 1989 now abandoned.

BACKGROUND OF THE INVENTION

1. Field of the Invention

This invention relates to systems for the detection of explosives and other controlled substances such as drugs or narcotics. More particularly, the present invention relates to an integrated system consisting of a sampling chamber, a detection system, and a data processing system, for the detection of the vapor and/or particulate emissions of explosives and controlled substances in a non-invasive manner.

2. Discussion of the Prior Art

In recent years there has been a steady increase in the illegal use of explosives as well as an increase in the transportation of contraband substances such as drugs or narcotics. It is impossible to detect the existence or prevent all of the cases of bombings and drug smuggling going on; however, it is possible to detect explosives and contraband substances in particular areas where high visibility and/or vulnerability exists such as in airports or airplanes. There are numerous ways in which an individual can place drugs or explosives on an airplane, and even more places an individual can hide the drugs or explosives once on the airplane. The illegal substances can be brought on the airplane by a knowing or unknowing individual by concealing the substance on his/her person or by placing the substances in baggage to be placed in the cargo section of the aircraft.

The methods for detecting substances such as explosives and drugs or narcotics have been studied for many years, and various techniques have been developed which range from explosives/drug sniffing dogs to highly sophisticated vapor detection devices. Basically, the detection of the aforementioned substances is accomplished in one of two ways; namely, non-vapor detection and vapor detection. Non-vapor detection methods include x-ray detection, gamma-ray detection, neutron activation detection and nuclear magnetic resonance detection. These methods of detection are more applicable to the detection of the various substances when the substances are concealed and are carried or associated with non-living items such as baggage to be carried onto an aircraft in that the detection techniques might pose a threat to living items. Vapor detection methods include electron capture detection, gas chromatography detection, mass spectroscopy detection, plasma chromatography detection, bio-sensor detection and laser photoacoustic detection. These methods of detection are more applicable to the detection of substances that are concealed and associated with living items such as those that can be carried by individuals including the residuals left on the individual who handled the various substances. All of the above methods are presently utilized, including explosive and drug sniffing dogs.

Today, there are many private and government research studies devoted to the development of systems and methods for the detection of explosives and drugs or narcotics. With the advances in explosives technology, such as the advent of the plastique explosives, which can be disguised as common items, it is becoming increasingly difficult to detect these substances. The problems that must be overcome in the detection of these substances as well as others, include low vapor pressure of the particular vapors escaping from the particular substance, the search time and the throughput of the various systems, the low concentration of vapor or particulate emissions from the particular substance, isolation of the particular substance with a high degree of reliability, and maintaining the integrity of the systems environment.

There is numerous prior art dealing with the technology of explosive and drug detection devices. The article "Air Flow Studies For Personnel Explosive Screening Portals" authored by R. L. Schellenbaum of Scandia National Labs which was published in 1987 as part of the Carnahan Conference on Securities Technology in Atlanta, Ga. (July 15, 1987) discloses a study on various types of integrated systems for the detection of contraband explosives. The study outlined a three step process, which includes the collection of vapor, preconcentration, and detection, for the capture and detection of the vapors emanating from explosive substances. The article discloses various types of collection devices for collecting the sample. Various portal configurations and air flow mechanics within each of the portals were studied to see which one provided the best sample. The Atmos-Tech Air Shower Portal, a Modified Atmos-Tech Portal and a Cylindrical Portal were used in the study with various air flow configurations. The study concluded that downward, semi-laminar flow over the body cross-sectional area combined with a vacuum flow collection funnel of approximately twelve inches in diameter placed beneath the grating in the floor of the portal was the best way to collect the explosives vapor or particulate emissions from an individual passing through the portal.

For the detection part of the study, various detection devices were used including the Phemto-Chem 100 Ion Mobility Spectrometer in combination with a preconcentrator developed by Ion Track Instruments Inc. The ion mobility spectrometer is a plasma chromatograph which uses an atmospheric ion-molecule reactor that produces charged molecules which can be analyzed by ion mobility. The preconcentrator comprises a motor-driven, metal screen disc rotated with a cast metal casing. The screen adsorbs the vapor and is then heated for desorption of the vapor. This adsorption-desorption process is the necessary preconcentration step which is used to increase the vapor and/or particulate concentration in the collected air sample.

The major problem encountered in the use of the portal detection systems in the study was maintaining the integrity of the sample air volume. In maintaining the integrity of the sample air volume, it is necessary to prevent the sample air volume to be contaminated with the ambient environment at the same time trying to maintain a steady flow of traffic through the portal, which is essential to efficient operation of any type of screening system in which heavy traffic is common place. The aforementioned article suggests that the integrity of the sample air volume was not maintained in portals without doors. If ambient drafts were present, such as those from air conditioners or just the flow of pedestrian traffic, a reduction of ten percent in detection was encountered. The addition of doors on the portals effected a rise in the detection rate; however, it produced unacceptable pedestrian traffic problems which would not meet the requirements for high throughputs required by airports.

In the patent art, there are a group of references which disclose various methods and devices for detecting contraband substances, including both drugs and explosives. These references are all directed to the detection of contraband substances within a container or luggage, and not those carried on a person. U.S. Pat. Nos. 4,580,440 and 4,718,268 both assigned to British Aerospace Public Company Limited disclose a method and apparatus for detecting contraband substances sealed in freight type cargo. Basically, the method consists of sealing the cargo in a container, agitating the cargo in order to shake off the vapor or particulate matter emanating from the cargo into the surrounding atmosphere, sampling the atmosphere, heating the collected sample and analyzing the sample utilizing gas chromatography. U.S. Pat. No. 4,202,200 assigned to Pye Limited discloses an apparatus for detecting explosive substances in closed containers. Basically, objects such as luggage are passed through a controlled axis tunnel wherein the objects are swept by circulating air flows, and then the air sample is collected and analyzed. It is also suggested that if a larger tunnel is constructed, people as well as objects can be passed through it. The aforementioned inventions provide a means and method for detecting contraband substances by using vapor sampling; however, none of the inventions provide or suggest the use of a preconcentrator means for increasing the sensitivity and selectivity of the detection means. Additional patent references which disclose similar type systems are U.S. Pat. Nos. 3,998,101 and 4,111,049.

There are numerous patent references in the testing and monitoring art which disclose a concentration step which includes the filtration or absorption of the molecules of interest over time. After a predetermined period of exposure, the filtering/absorption media is removed and desorbed with heat, while a new filter/absorption media is placed in the air stream. U.S. Pat. No. 3,768,302 assigned to Barringer Research Limited discloses a system used in the geological testing area and in which the system receives an air stream containing particulates. The sample undergoes a concentration step which includes passing the air sample over two paths with adsorbing/desorbing steps, and finally analyzed. U.S. Pat. No. 4,056,968 assigned to the same assignee as the above patent also discloses a system which is also used in the geological testing area. In this invention, the concentrated molecules could be desorbed from a moving tape as well as from a moving disk. U.S. Pat. No. 4,775,484 discloses a rotating filter media which is used to absorb particulate material during one stage of its rotation, and which is purged or cleaned at a separate and second stage of its rotation. U.S. Pat. No. 4,127,395 also discloses a common absorption/desorption circuit using a pair of absorbent media, wherein one of the pair is absorbing, while the other is desorbing. U.S. Pat. Nos. 3,925,022, 3,997,297 and 3,410,663 all disclose absorption/desorption type devices. All of the aforementioned devices disclose systems for the absorption and subsequent desorption of particulate or vapor matter; however, none disclose a portal type sampling chamber.

SUMMARY OF THE INVENTION

The present invention is directed to a system for the detection of explosives, chemical agents and other controlled substances such as drugs or narcotics by detecting their vapor and/or particulate emissions. The system comprises a sampling chamber, a vapor or particulate concentrator and analyzer, and a control and data processing system. The system is particularly useful in field environments, such as airports, where it can be used to detect the aforementioned substances on an individual or in the baggage of the individual. The system meets the requirement to detect the aforementioned substances in a non-invasive manner at any required level, and to do it so quickly that the free passage of people and baggage is not unduly interrupted.

The sampling chamber is a portal with internal dimensions of approximately six feet in length, seven feet in height and three feet in width. The dimensions of the portal are such as to allow an average sized individual as well as a wheel chair bound individual to easily pass through. The portal is designed in such a way as to have an internal air flow sweep over an individual walking or passing through the portal at a normal walking pace, and at the same time have the air sample swept from the individual contain a meaningful concentration of vapors or particulate matter to be analyzed. To accomplish this, the sampling chamber or portal is designed with a unique geometry and contains air guides or jets for providing an air flow which effectively isolates the internal air volume from the ambient environment while efficiently sweeping the individual passing through the portal. The air volume or sample inside the portal is collected through a sampling port located within the ceiling section of the portal. The air sample is then transported to the sample collector and preconcentrator (SCAP).

The sampling chamber or portal is capable of collecting and delivering to the SCAP vapor and/or particulate matter when they are present in as low a concentration as several parts per trillion of ambient air. The SCAP, through a series of steps of decreasing sample volume and increasing sample concentration, delivers a concentrated sample to a fast response chemical analyzer which may be either a gas chromatograph/electron capture detector or an ion mobility spectrometer or both. The principle of operation of the SCAP is one of adsorbing the sample onto a selected substrate with subsequent selective thermal desorption. This process is repeated through a series of steps of decreasing sample volume and increasing sample concentration. Upon completion of the preconcentration steps, the purified sample material is analyzed by the aforementioned devices wherein the analysis consists of identifying the various materials and determining the amount of material present.

The total system and all system processes are controlled by a control system which comprises a digital computer and associated software. The system is configured and controlled to make all required measurements and prepare the results in a usable and intelligible format. The control system controls the collection of vapors, the preconcentration and analysis steps, and the data analysis and data formatting. In addition, the computer continuously performs self diagnostic and self calibration procedures on the total system and alerts the user to any potential problems.

The system for the detection of explosives and other controlled materials of the present invention provides for the efficient detection of explosives, chemical agents or other controlled materials such as drugs or narcotics by detecting the vapor and/or particulate emissions from these substances. The vapor or particulate emissions can come from substances concealed on the individual, the individual's baggage, or from a residue left on an individual who handled the particular substance. The present invention provides a system with a high degree of sensitivity and selectivity to a wide range of substances. The high degree of sensitivity and selectivity is accomplished by employing a system which utilizes the combination of a unique geometry portal with aerodynamics that prevent the cross-contamination of air within the portal with that of the ambient environment and a multi-stage preconcentrator that decreases sample volume while maximizing sample concentration thereby allowing much larger sample volumes to be taken as well as much shorter sample collection times. The system provides a high reliability rate which is accomplished by utilizing the computer control system for automatic calibration and self diagnostic procedures. In addition, the system provides a high degree of versatility in that by changing the programming of the computer, a wide range of explosives, controlled chemical agents, and drugs and narcotics which have differing physical and chemical properties can be detected. Having the total system under software control provides a more versatile system and one that is easily reconfigurable.

The present invention has a wide variety of applications where a high throughput of people is required. In airports, the detection of explosives and controlled substances is of paramount importance due to the rise in terrorist attacks and drug smuggling. The present invention allows for the fast and reliable detection of the aforementioned substances in a non-invasive manner in a variety of field environments such as in airports. The system of the invention is applicable where the detection of concealed substances is absolutely required.

BRIEF DESCRIPTION OF THE DRAWINGS

For the purpose of illustrating the invention, there is shown the drawings the forms which are presently preferred; however, it should be understood that the invention is not necessarily limited to the precise arrangements and instrumentalities here shown.

FIG. 11a is a diagrammatic diagram of the portable sample collector of the present invention;

FIG. 11b is a diagrammatic representation of the luggage sampling means of the present invention;

FIG. 13 is a block diagram of the control and data processing system of the present invention;

FIG. 15 is a time chart indicating the various time durations of the processes associated with the screening process

DESCRIPTION OF THE PREFERRED EMBODIMENT

Figure 2:
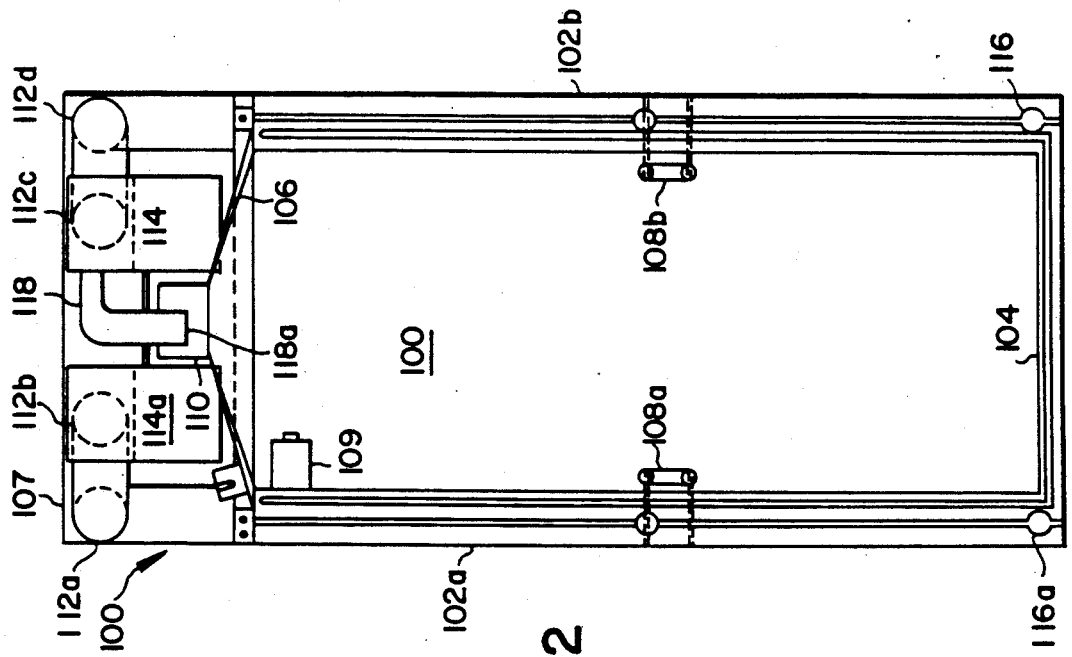
FIG. 2 is a sectional end view of the sampling chamber of the present invention taken along section lines 2-2' in FIG. 1.

The explosive detection screening system of the present invention is designed to detect explosives, chemical agents or other controlled materials such as drugs or narcotics by detecting their vapor or particulate emissions. These substances are assumed to be concealed on individuals or in their baggage in airports or other high vulnerability, high visibility environments. It is necessary to detect these substances in a non-invasive manner at any required level, and to do it so quickly that the free passage of people and baggage is not unduly interrupted. The system is an integrated system comprising a sampling chamber, a vapor and/or particulate concentrator and analyzer and a control data processing system.

The sampling chamber is a portal in which internally generated air flows, sweep the vapor and/or particulate emissions emanating from an individual or object passing through the chamber to a collection area. The sampling chamber is designed in such a way as to capture a high enough concentration of emissions so as to be able to detect the presence of the aforementioned substances with a high degree of reliability and dependability. The internal volume of air is recirculated with a small amount being removed at the sampling time. At the sampling time, an external air pump or fan draws a sample of the collected air volume into a sample collector and preconcentrator (SCAP).

The sampling chamber is capable of collecting and delivering to the SCAP vapors when they are in as low a concentration as several parts per trillion of ambient air. The SCAP, through a series of steps of decreasing sample volume and increasing sample concentration, delivers a concentrated sample to a fast response chemical analyzer which may be either a gas chromatograph/electron capture detector or an ion mobility spectrometer or both. Using this multi-stage concentration process of adsorption and desorption, much larger sample volumes can be processed with high degrees of sensitivity and selectivity. The data collected is then assimilated and analyzed by a digital computer which is part of the control system which operates and controls the total system.

The control system is a control and data processing system of which the primary requirement is to report the presence of, and if required, the level of a specified substance. The system must be capable of distinguishing between background levels of a substance and alarm levels. The system also controls the operation of the entire system by automatic control methods which is run by a microprocessor or digital computer. The control system is easily reprogrammed to detect various substances because of modularized programming techniques.

SAMPLING CHAMBER

The sampling chamber for people is a portal that is designed in such a way that as a person walks through this chamber, at a normal walking pace, an internal air flow carries a sample of vapors and/or particulate matter from them to a sampling port where it will be collected for analysis. There are three major design requirements that the chamber was designed to meet. First, the sampling chamber must gather a meaningful sample of the environment surrounding a person or object passing through the chamber. In considering a solution to the problem posed by the first design requirement, it is necessary to consider that the sampling chamber must be large enough for an average size individual to comfortably pass through the chamber; therefore, there is a considerable volume of air located within the chamber resulting in possibly only several parts vapor or particulate emission per trillion parts of air or possibly even less. The solution to this problem of dilution is to design the chamber long enough so the individual or object passing through the chamber remains in the chamber for a duration of time so as a meaningful sample of the environment can be gathered. Second, for the purposes of sensitivity, selectivity and preventing cross-contamination of the sample to be analyzed, the sample to be collected must be isolated as much as possible from the ambient environment. In considering a solution to the problem posed by the second design requirement, it is necessary to once again consider the problem of dilution caused by having a larger chamber. Since there already exists a dilution problem, the chamber must be designed with a unique geometry and internal aerodynamics so as to prevent further dilution and contamination by the mixing of internal air with the ambient air to the greatest extent possible. The third design requirement is that the sample must be gathered in as complete form as possible in as short as time as possible. In considering a solution to the problem posed by the third design requirement, it is necessary to consider the problems and solutions considered above and find a balance between them. The time an individual or object spends in passing through the chamber must be long enough so as to gather a meaningful sample, but not long enough to cause unduly long pedestrian traffic delays. Secondly, since there is a dilution problem, the chamber was designed in a unique way so as to prevent cross-contamination with the ambient environment, and this unique design must not prevent the normal flow of traffic; therefore, the aerodynamics discussed in the solution to the second problem must be such that the meaningful sample is gathered quickly.

Figure 1:
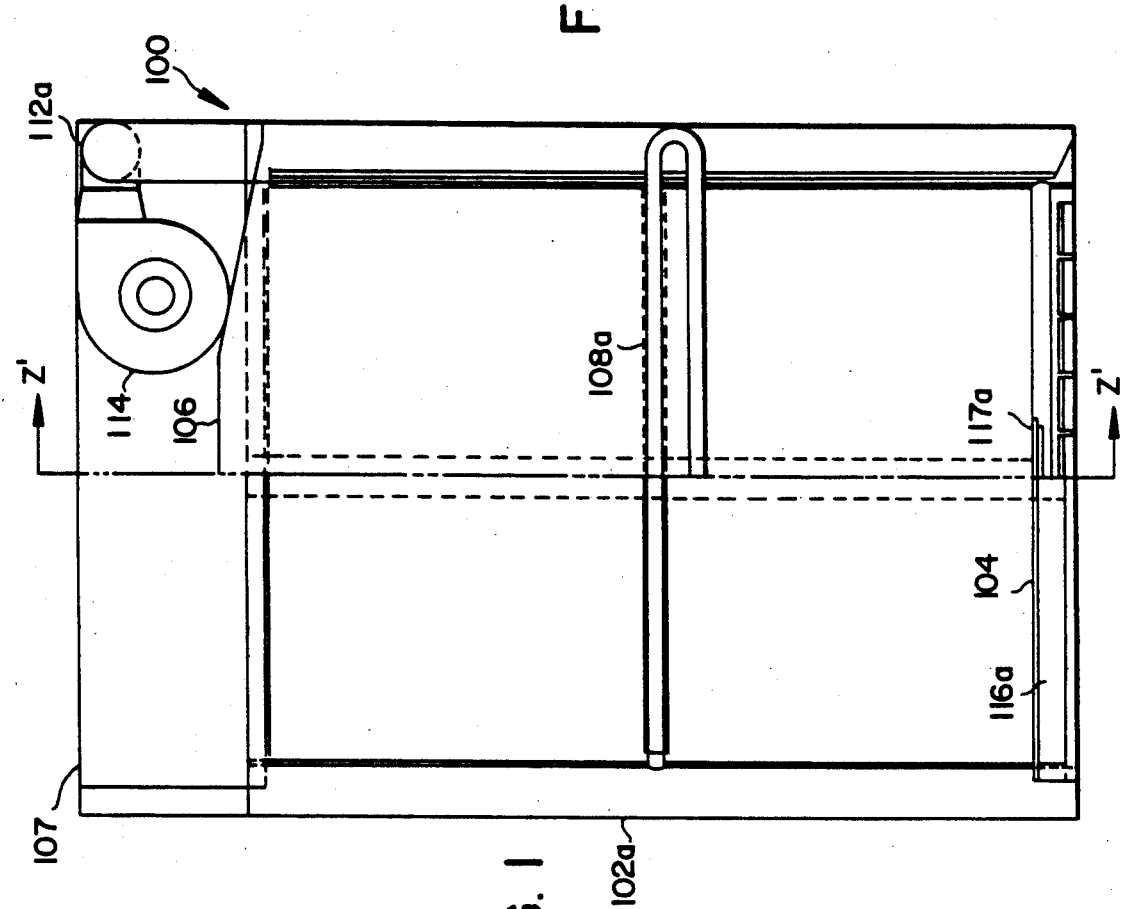
FIG. 1 is a sectional side view of the sampling chamber of the present invention.

Referring to FIGS. 1 and 2, there is shown a sectional side view and end view of the sampling chamber 100 or portal. The sampling chamber 100 has a rectangular geometry having internal dimensions of approximately six feet in length, seven feet in height, and three feet in width. These dimensions allow an average size individual, walking at an normal walking pace to remain in the chamber 100 for approximately two to three seconds which is enough time to gather the aforementioned meaningful sample. The rectangular chamber 100 has two walls 102a and 102b, which run the length of the chamber 100, a floor 104, a convergent or conically shaped ceiling 106 the importance of which will be discussed subsequently and a roof 107. In order to maintain the uninhibited flow of pedestrian traffic through the chamber 100, no doors and only two walls, 102a and 102b, were used. Hand rails 108a and 108b attached to walls 102a and 102b respectively are provided to aid individuals in passing through the chamber 100 quickly and safely. The floor 104 of the chamber 100 is not a necessary component, and in other configurations it is not utilized. The chamber 100 can be constructed utilizing a variety of materials including aluminum and plastics; however, clear materials such as plexiglass or fiberglass is preferred so individuals passing through the chamber 100 can be observed. In addition, a video camera 109 may be utilized to capture an image of the individual passing through the chamber 100 which will be electronically stored along with the collected data.

The sampling chamber 100 operates on an air recirculating principle and the only air removed from the internal recirculating volume is a comparatively small amount leaving by sampling port 118a. The internal air volume is circulated through internal air flow guides or jets and is collected by collection duct 110 which is a 16"×20"×6" rectangular duct connected to the center of the conical ceiling 106 and which empties into the space created between the ceiling 106 and the roof 107. This results in a large volume of controlled recirculating air flow capable of delivering a vapor and/or particulate sample from anywhere in the chamber 100 to the sampling port 118a in approximately one second.

Figure 3:
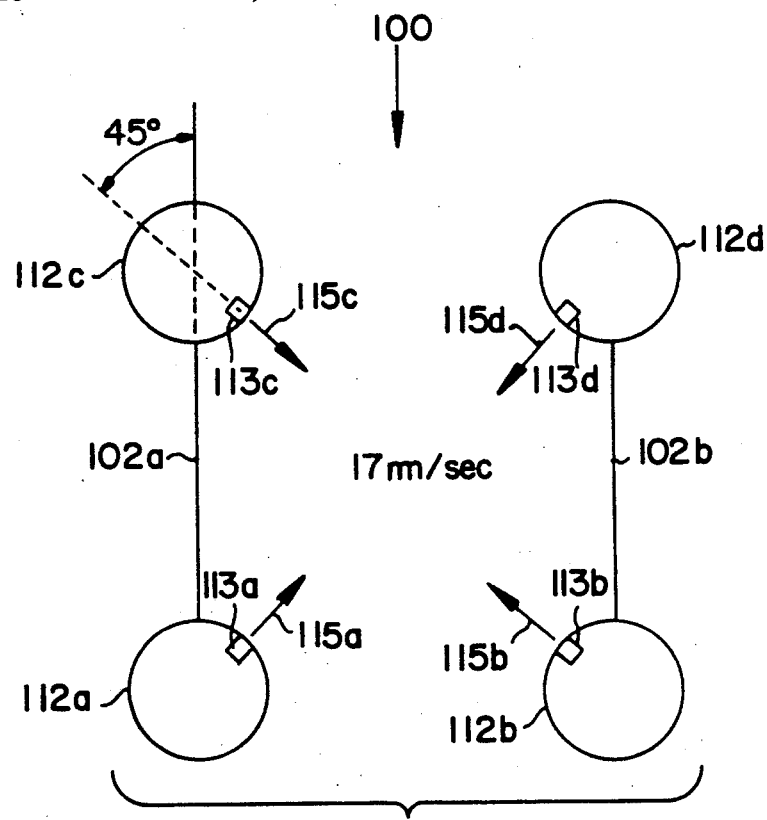
FIG. 3 is a top view of the sampling chamber of the present invention.
Figure 4:
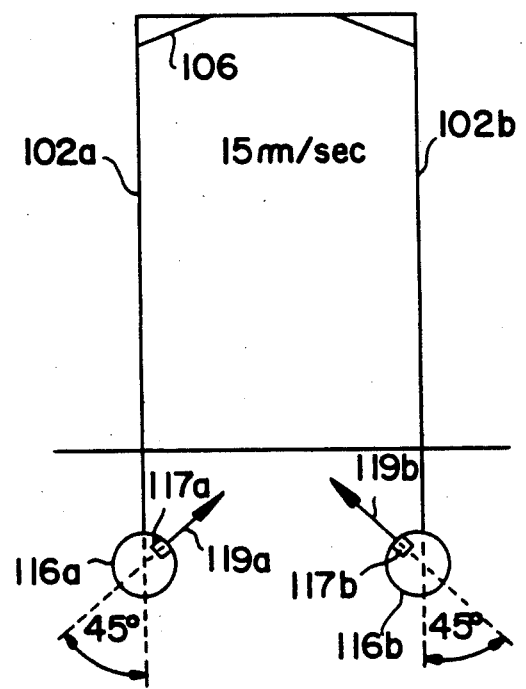
FIG. 4 is an end view of the sampling chamber of the present invention.

The conical ceiling 106 aids in the collection of the sample volume by creating an inverted funnel for the air sample flow which serves to concentrate a larger volume of air across a small cross section for sampling purposes. A dynamic low pressure zone is created in the region of the collection duct 110 when the air is drawn through the collection duct 110 into the ceiling plenum by four exhaust fans two of which are shown in FIG. 2 as 114, and 114a. In each corner of the chamber 100, there are six inch diameter end columns 112a–d. Each of the four end columns 112a–d are mounted vertically in the chamber 100 and run from the floor 104 to the ceiling 106. Each column 112a–d has six slots of one foot in length and a half inch in width 113a–d as shown in FIG. 3, which is a top view of the chamber 100, with inch and a half internal guide vanes (not shown) for directing the air flow at a forty-five degree angle towards the center of the chamber 100 as shown by arrows 115a–d in FIG. 3. The air flow through the columns 112a–d is provided by four independent fans, two of which are shown in FIG. 2 as fans 114 and 114a. The four fans are mounted in the chamber 100 above the conical ceiling 106 and below the outer roof 107. Each fan is connected to one of the end columns 112a–d and provide 1000 CFM of air to each column 112a–d resulting in an air velocity of 17 m/sec, in the directions indicated by arrows 115a–d, from the guide vanes of the columns 112a–d as shown in FIG. 3. The suction side of the fans are open to a common plenum located in the same space that the fans occupy. In addition to these inwardly directed vertical air jets 113a–d there are two upwardly directed air guides 117a and 117b or jets located in side air flow pipes 116a and 116b which are mounted along the floor 104 and against walls 102a and 102b. The side flow pipes 116a and 116b are connected to end columns 112a–d and receive air from them. In each side flow pipe 116a and 116b there are twelve inch by half inch air slots 117a and 117b located in the center of each pipe and directed towards the center of the chamber at a forty-five degree angle as shown in FIG. 4. The air velocity of the air leaving side flow pipes 116a and 116b is 15 m/sec in the direction indicated by arrows 119a and 119b. The combined effect of the air flow created by the end columns 112a–d and the side flow pipes 116a and 116b is a dynamic high pressure region created in the center region of chamber 100. The recirculating fans which draw air through collection duct 110 create a dynamic low pressure zone within chamber 100, which creates a net air flow up towards the collection duct 110. This air flow is the flow that sweeps individuals or objects passing through the chamber. The effect of the high pressure region and the low pressure region created by the exhausting of the air sample through conical ceiling 106 and into the collection duct 110 is a balance of atmospheric conditions which results in very little external air entering or leaving the chamber 100. Basically, the high pressure region inhibits air from entering the chamber 100. The majority of the moving air mass goes through the collection duct 110 and to the common plenum where it will once again be used by the four fans to recirculate the internal volume of the chamber 100. A portion of the recirculated air is collected through a sampling port 118a, which is the open end of a stainless steel pipe 118 which is used to transport a selected sample from the chamber 100 to the second stage of operation; namely, the preconcentration stage which shall be discussed subsequently.

The four end columns 112a–d and the two side air flow pipes 116a and 116b represent one embodiment for delivering the air supplied by the four independent fans as separate and directional air jet streams. The fans can be connected to various types of air ducts or plenums with guide vanes or nozzles to form the exiting air into jet streams. In addition, partioned hollow walls also with guide vanes or nozzles can be used as an alternate approach for forming the air from the fans into separate and directional air jet streams. The manner in which the air flow is supplied to the guide means and the manner in which the jet streams are formed is not critical; however, the specific directions of the jets streams are. It is important that the proper angle and orientation of the jet streams be maintained so as to provide a net flow of air capable of sweeping an individual or object passing through said sampling chamber means 100 while maintaining the integrity of the volume of air within the sampling chamber means 100.

Figure 5:
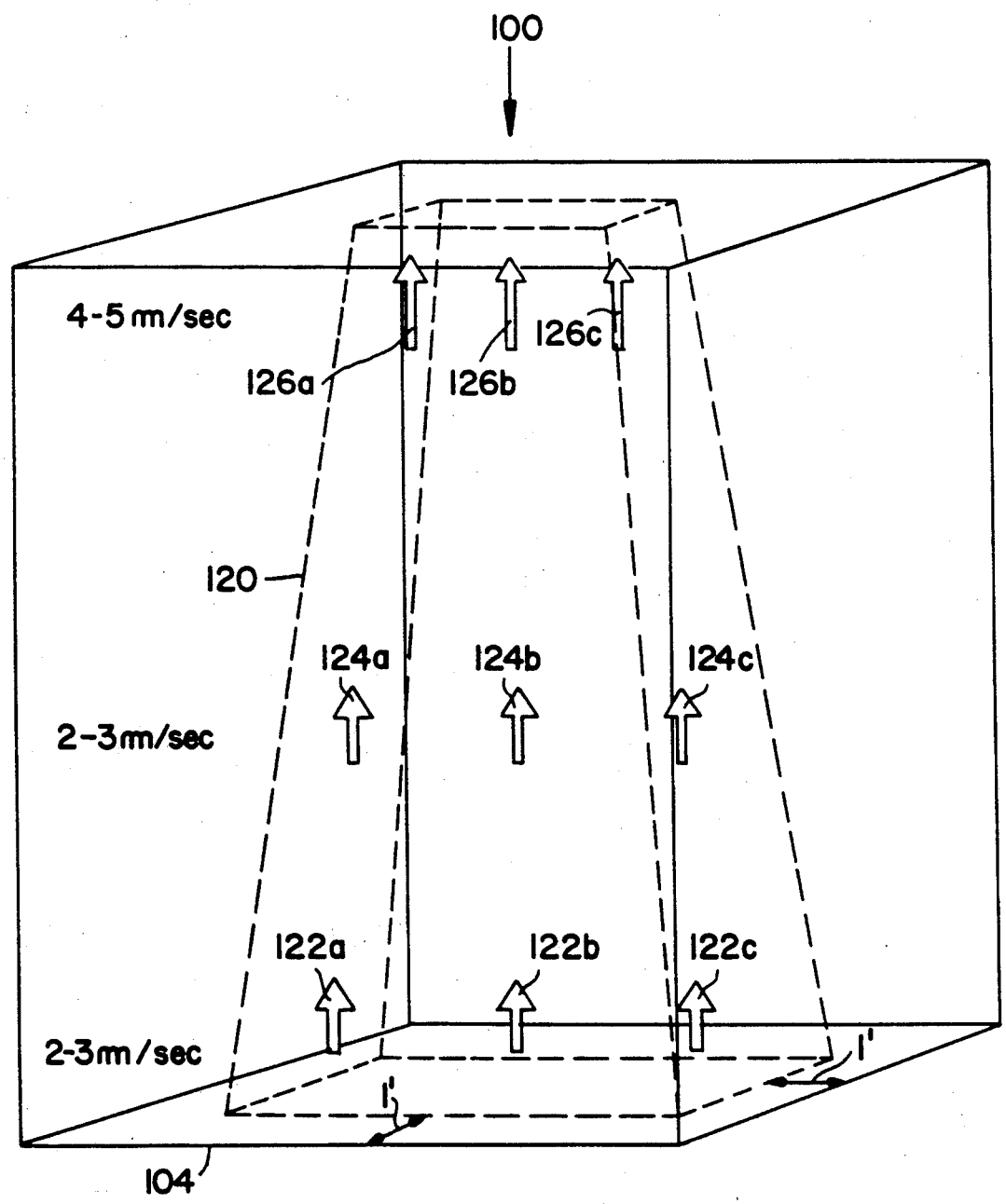
FIG. 5 is a diagrammatic representation of the flow of air within the sampling chamber of the present invention.

Referring now to FIG. 5, the volume of air 120 enclosed by the dashed lines indicates the total volume of air moving towards the collection duct 110 and sampling port 118a shown in FIG. 2. The upward flow of air starts at approximately one foot in from the perimeter of the chamber floor 104. This figure indicates the net upward flow of air, and does not intend to exclude other air currents present in the chamber, because other currents are present; however, their direction is not upward. As can be seen in FIG. 5, the effect of the generated internal air flow and the shape of the ceiling 106 shown in FIG. 2 tends to focus or concentrate the large volume of air flowing upwards to a smaller, but more concentrated volume of air. Arrows 122a–c, 124a–c and 126a–c indicate the velocities of the air mass at different stages in the flow. In the lower to middle regions, the air flow is 2–3 m/sec, and as the air mass approaches the low pressure region, the velocity increases to 4–5 m/sec.

Figure 6:
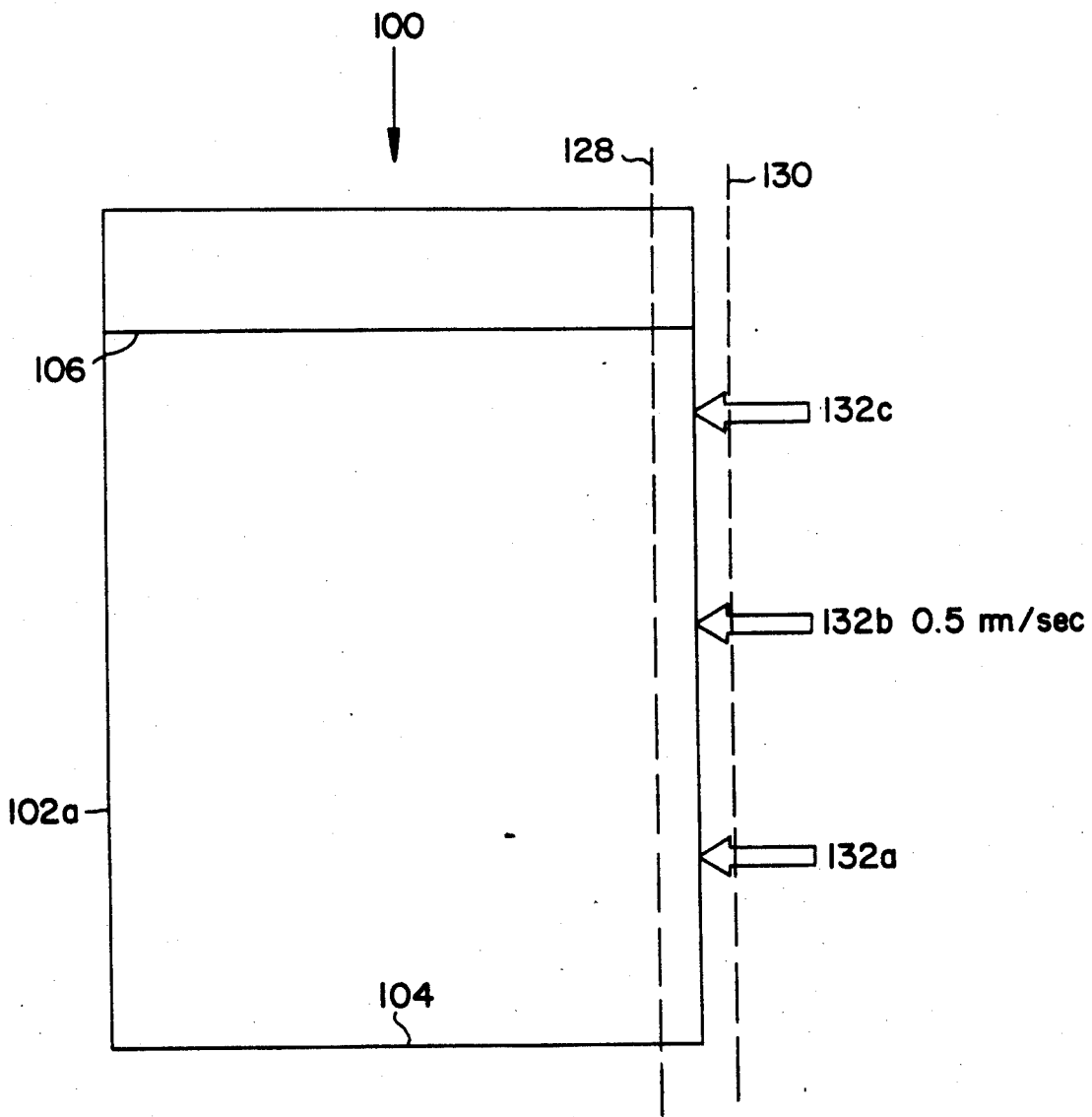
FIG. 6 is a diagrammatic sectional view of the internal/external air boundary that exists at the end of the sampling chamber of the present invention.

Turning to FIG. 6, a diagrammatic side view of the chamber 100 is shown. The region indicated by the dotted lines 128 and 130 indicate the region in which cross-contamination of the internal air volume with the ambient environment occurs. As indicated by arrows 132a–c, air from the surrounding environment enters the chamber 100 at approximately 0.5 m/sec. The air from the outside environment is drawn in by the aerodynamics created by the internal air flow. This air flow into the chamber 100 results in one half of the internal air to be exchanged with the outside air in approximately 30 seconds. Since the collection time takes approximately one second, the cross-contamination is minimal. The only way to maintain absolute integrity of the internal air volume is to provide rotating doors with a seal, and this however, would result in undesirable time delays.

SAMPLE COLLECTOR AND PRECONCENTRATOR

The sample collector and preconcentrator (SCAP) is used as part of the overall system to enchance overall system sensitivity and selectivity. In general terms, the SCAP must simply discard, in a multi-step process, non-required molecules of air while not losing the targeted molecules of interest. In the sample collection and preconcentration step, the targeted materials are adsorbed onto a selected substrate, and then selectively desorbed. This process is repeated through a series of steps which decrease sample volume and increase sample concentration.

Figure 7:
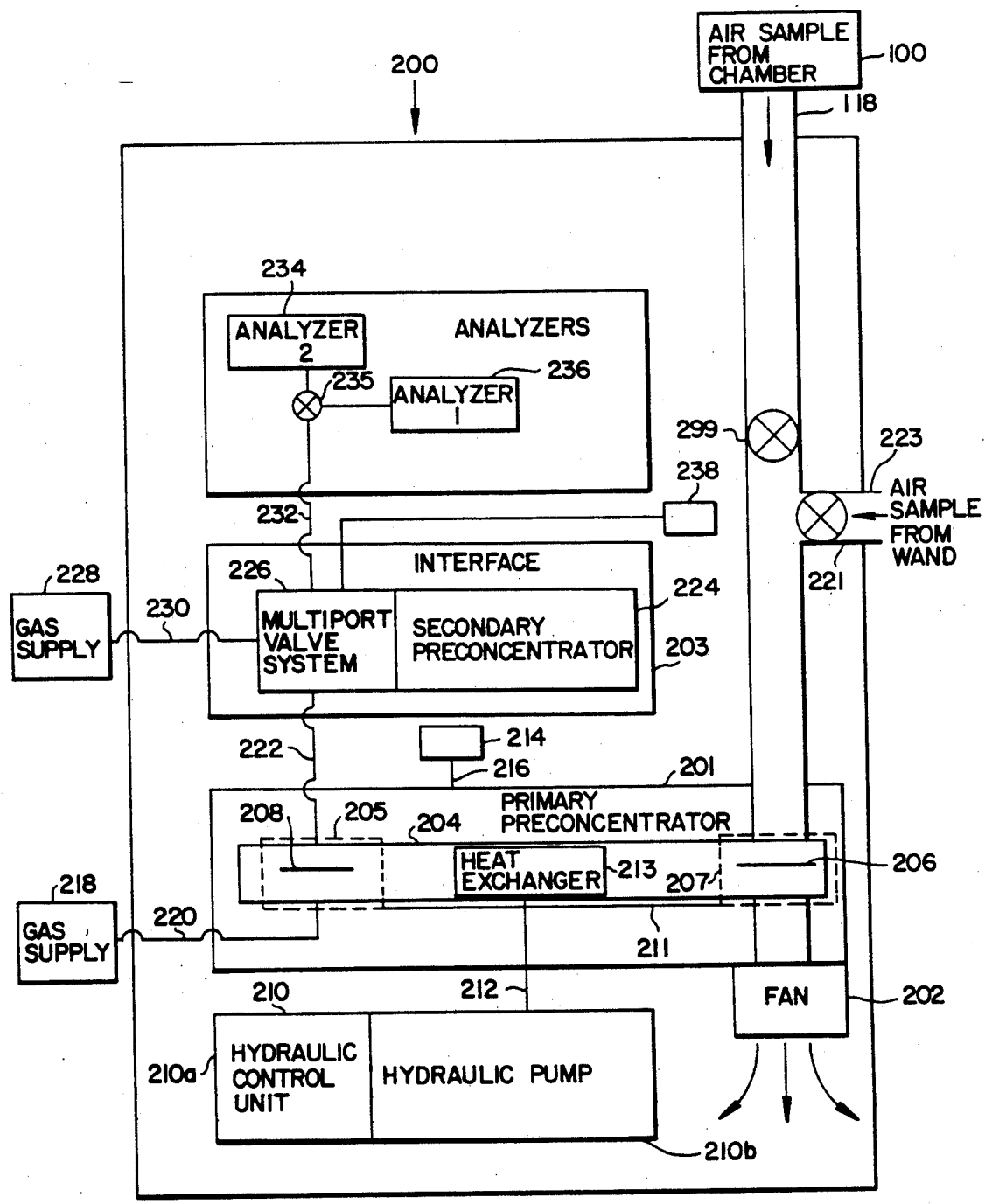
FIG. 7 is a diagrammatic block diagram of the sample collector and preconcentrator of the present invention.

As illustrated in FIG. 7, the SCAP 200 is supplied with sample air by pipe 118 which extends to the sampling chamber 100. During sampling periods a high suction fan 202 draws the sample volume through the sampling port 118a. The fan 202 is connected to pipe 118 on the suction side with the discharge side connected to a vent or exhaust system to the ambient environment.

The first stage of the concentration process involves the primary preconcentrator 201 which consists essentially of a rotating filtering means 204. The air sample drawn from the sampling chamber 100 is drawn through filtering means 204. The filtering means 204 consists of two interconnected filtering elements 206 and 208. The filtering elements 206 and 208 are wire screens which hold an adsorbing material. Each filtering element 206 and 208 may be rotated through either of two positions. Position 1 is in line with pipe 118 and position 2 is in line with a secondary preconcentrator 203. The positions of the filtering elements 206 and 208 are changed by a control system which in this embodiment is a hydraulic actuation system 210 which is connected to filtering means 204 by shaft 212 which lifts movable platform 211 to move each of the filter elements into a sealed connection at position 1 and at position 2. A preconcentrator control unit 214 is also connected to filtering means 204 by shaft 216. The hydraulic actuation system 210 is comprised of a hydraulic control unit 210a and a hydraulic pump 210b and is operable to lower and raise holding elements 205 and 207, into the unlocked and locked positions respectively. When it is time to rotate the filters 206 and 208, hydraulic actuation system 210 lowers holding elements 207 and 205 which engage filter elements 206 and 208 respectively. Upon engagement of the filter elements 206 and 208, preconcentrator control unit 214, which is a computer controlled stepper motor, is operable to rotate filtering elements 206 and 208 between positions 1 and 2 via shaft 216. The control of the hydraulic actuation system 210 and the preconcentrator control unit 214 is accomplished via the control system which will be fully explained in subsequent paragraphs.

Figure 8:
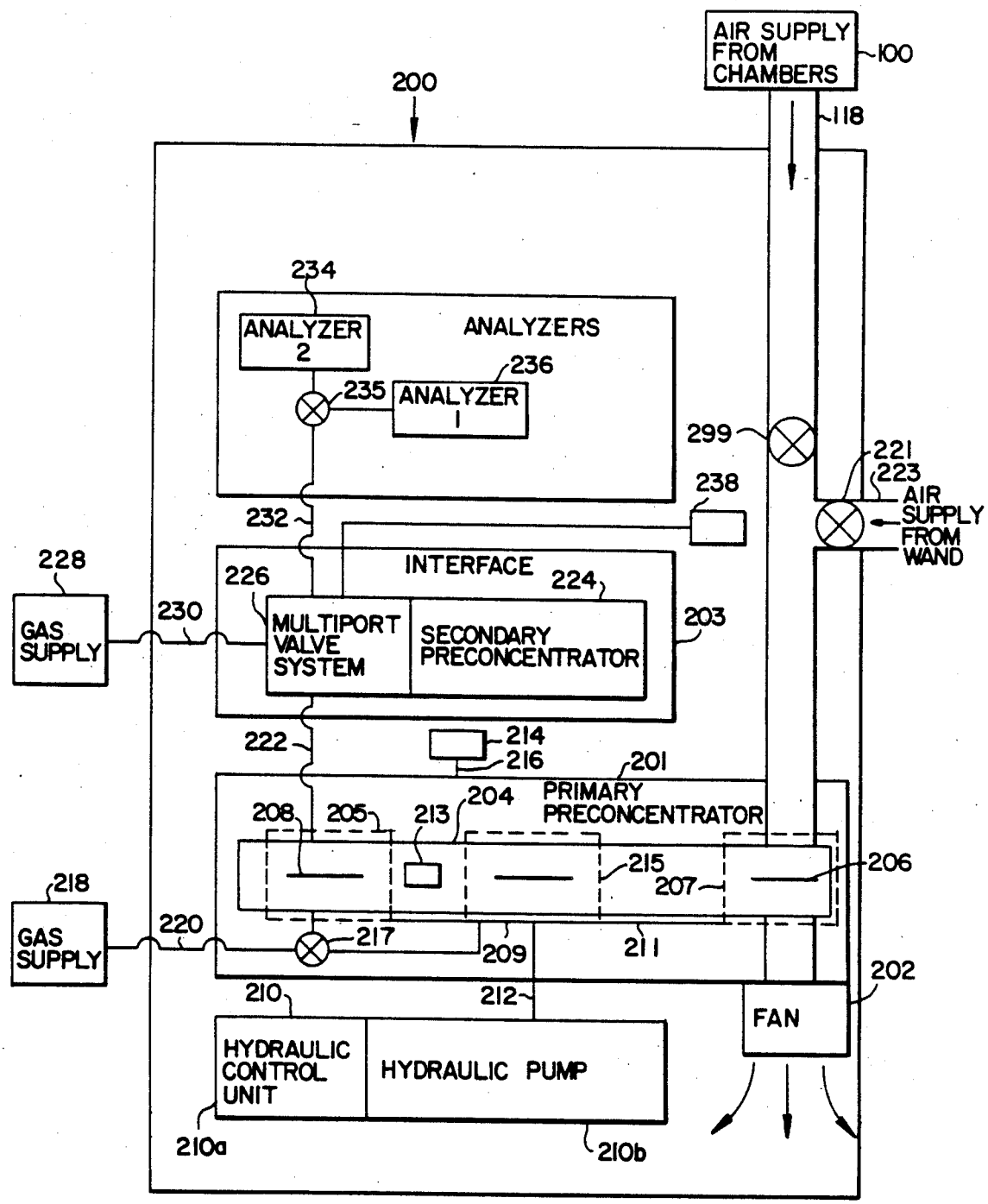
FIG. 8 is a diagrammatic block diagram of the sample collector and preconcentrator of the present invention with a three filter configuration.
Figure 9:
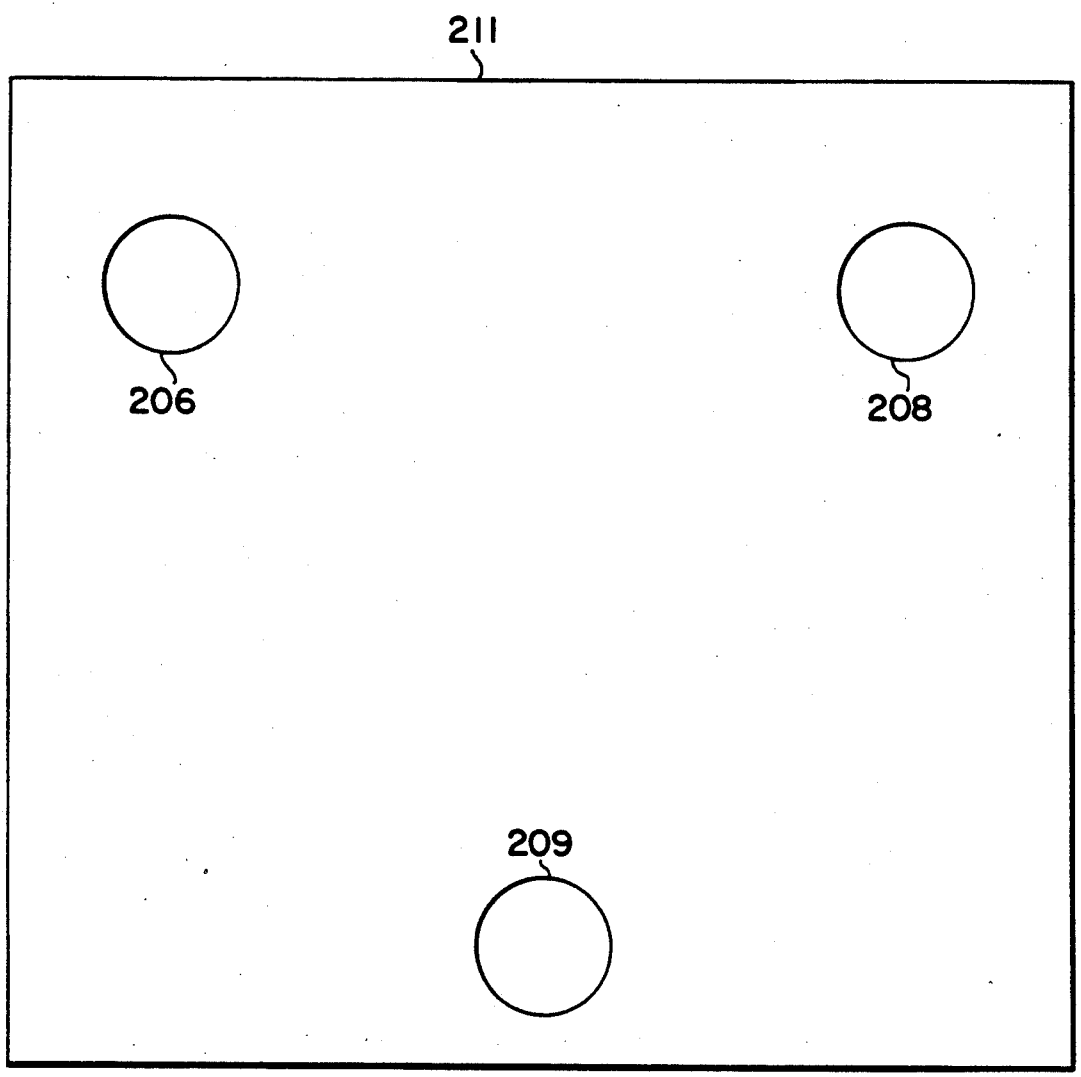
FIG. 9 is a plane view of the three filter configuration of the primary preconcentrator of the present invention.

In a second embodiment the filtering means 204 consists of three interconnected filtering elements 206, 208 and 209 as shown in FIG. 8. Filter element 209 like filter elements 206 and 208 is a wire screen which holds the adsorbing material. Each filtering element 206, 208 and 209 may be rotated through either of three positions. Position 1 is in line with pipe 118, position 2 is in line with a secondary preconcentrator 203, and position 3 is exactly in between position 1 and position 2. FIG. 9 shows a plane view of the three filter elements 206, 208, and 209 spaced 120 degrees apart on movable platform 211. The positions of the filtering elements 206, 208 and 209 are changed by a control system which in this embodiment is a hydraulic actuation system 210 which is connected to filtering means 204 by shaft 212 which lifts movable platform 211 to move each of the filter elements into a sealed connection at position 1, into a sealed connection at position 2 and at position 3. The hydraulic actuation system 210 is comprised of a hydraulic control unit 210a and a hydraulic pump 210b and is operable to lower and raise holding elements 205, 207 and 215 into the unlocked and locked positions respectively. When it is time to rotate the filters 206, 208 and 209, hydraulic actuation system 210 lowers holding elements 207, 205 and 215 which engage filter elements 206, 208 and 209, respectively. Upon engagement of the filter elements 206, 208 and 209, preconcentration control unit 214, which is a computer controlled stepper motor, is operable to rotate filtering elements 206, 208 and 209 between positions 1, 2 and 3 via shaft 216.

Referring now to FIG. 7, the two filter process is described. During a sampling period which is controlled by the control system, fan 202 draws the sample from the chamber 100 and through filter element 206 which is position 1. Filter element 206 collects the vapor and/or particulate matter contained in the air sample on an adsorption substrate. The filter element 206 comprises an adsorber that is selected to have enhanced adsorption for the target materials and lessor adsorption for any contaminants. When the air sample passes through the filter element 206 containing the adsorber, the adsorber preferentially selects a sample of the target materials, and other contaminants are passed on to be vented or exhausted by fan 202. Upon completion of the sampling period, and adsorption of the target materials onto filter element 206, filter element 206 is switched to position 2 by the preconcentrator control unit 214 and raised into a locked position by the hydraulic actuation system 210 so the desorption of the target materials can occur.

In the desorption process, a stream of pure gas is passed over the adsorber containing the target materials and any remaining contaminants. The pure gas, which is usually an inert gas, is supplied from a gas supply 218 and transported to position 2 of filter means 204 by gas line 220. This pure gas flow is much smaller then the volume of air used in the sampling chamber 100. The temperature of the adsorber is raised in a controlled fashion by the control system, illustrated in FIG. 13. The temperature of the filter being desorbed is raised by either a heat exchanger 213 or by the temperature of the pure gas from source 218. If the temperature of the filter being desorbed is raised utilizing the pure gas, then the gas flow is diverted to a heating element (not shown) where it is raised to the proper temperature. When the desorption temperature for the target material is reached, the temperature is held constant and the pure gas flow is quickly switched to the desorption stage in the concentration process. The heated gas then absorbs the target materials and carries them on to the next stage. The gas flow containing the target materials is routed to the secondary preconcentrator 203 or interface unit via gas line 222. As the desorption process is rapid, only a small volume of gas is transferred which results in the next stage receiving the target materials in a concentrated form.

The primary concentration of the target materials is a continuous two step process because of the two filter elements 206 and 208 both contain adsorbing substrates. When filter element 206 is adsorbing the target materials, filter element 208 is in the desorption process. Upon completion of the desorption of the target materials from element 208, the adsorbing material of element 208 is purified from materials and contaminants and thus ready to be used as the adsorber in position 1. While a pair of rotating filter elements is illustrated in FIG. 7, it would also be possible to use single use strip media which traverses from the absorbing station to the desorbing station, or to hold the position of the filters fixed and alternate the sample and purge air streams to absorb and desorb the target materials.

Referring to FIG. 8, the three filter process is now described. In a second embodiment for the primary preconcentrator 201, a third filter element 209 is added, thus making the primary concentration of the target materials a continuous three step process, because the three filter elements 206, 208 and 209 all contain adsorbing substrates. When filter element 206 is adsorbing the target materials, filter element 208 is in the desorption process, and filter element 209 is be added to provide for a thermal cleansing of any vapors or particulates which may remain after the desorption process. When a particular filter element is in position 3, the pure gas supplied from gas supply means 218 is routed to position 3 of filter means 204 by gas line 220. The gas flow further sweeps the particular filter element in an attempt to further purify the adsorbing material from contaminants. The exiting gas with contaminants is exhausted to the ambient environment. A valve 217 is located in line with gas line 220 and is operable to switch the gas flow from position 2 to position 3 and vice versa.

The treatment of particulates and gaseous materials is slightly different at the first step of the concentration process. The particulates may be small particles or droplets of the target material itself or small particulates or droplets attached to dust particles or other vapor droplets. For particulates, the first stage is a filter or screen having selective adsorption characteristics in the path of the sample air flow from the sampling chamber 100. The particulates are physically trapped or adsorbed on this filter, and then the filter, or a portion of it, is physically transferred to a heated chamber and rapidly heated to a temperature that is sufficient to vaporize without decomposing the target particulates. A small quantity of heated pure carrier gas is admitted to the chamber to carry the now vaporized material to the next stage of the process. As stated previously, the heated gas can be used for supplying the heat for vaporization.

It is usually the case that the filter used in the sampling air flow for particulate materials is also the absorber for gaseous materials and therefore, as is shown in FIG. 7 a single primary preconcentrator 207 can be used to capture both particulate materials and gaseous materials. It is necessary to sample target materials as particulates because certain target materials may have too low a vapor pressure at room temperature to be sampled as gas or vapor. In addition, it is possible that the target material itself has a tendency to be present in the sample volume as an adsorbate on particulate material independent of vapor pressure considerations.

In the subsequent stages of concentration the selectable adsorbers are fixed and confined to metallic tubes. The sample and purge carrier gas flows are manipulated by switching valves which are under computer control. Referring once again to FIG. 7, the primary preconcentrator 201 is connected to the interface 203 by gas flow line 222. The interface 203, contains a secondary preconcentrator 224 and a multiport valve system 226. The purpose of the multi-port valve system 226 is for switching between the gas supply line 230 which is supplied by gas supply 228, the preconcentrator 224 adsorption tubes, the gas flow line 222 from the primary preconcentrator 201 and the gas flow line 232 to the chemical analyzers 234 and 236. Basically, the multi-port valve system 226 is a switching network. The secondary preconcentrator 224 is a series of adsorption tubes. The multi-port valve system 226 is driven by an interface control unit 238 which is simply a stepper motor to rotate the valves in the multiport valve system 226 when commanded to do so by the computer. The interface 203 represents a generic block of secondary preconcentrators, and thus one can cascade a series of multiport valve systems and adsorption tubes in an attempt to further purify the sample to be analyzed.

The adsorber tubes are very rapidly heated to and held at the selected predetermined temperature by heating the surrounding metallic tube. This is usually done by passing a controlled electrical current through the tube and using the tube itself as the heating element. In the case of larger adsorbent containing tubes, for the heating times of tens, to a very few hundreds of milliseconds, this current may be several hundred amperes. The temperature may be measured by brazing a tiny, very low mass thermocouple or thermistor to the tube. The thermocouple must be small enough so as not to affect the tube in any manner and it must be capable of responding rapidly. The thermocouple feeds the measured temperature to the computer of the control system wherein the computer controls the amount of current flowing through the tubes. Basically, the computer forms the digital closure of an analog control loop. The computer is used to monitor and control the temperature because the proper thermal program for the desired target materials or material is critical. The size of the tubes is decreased in steps to reflect the decrease in volume of gas containing the samples and may eventually reach the internal size of a capillary gas chromatograph column.

Figure 10A:
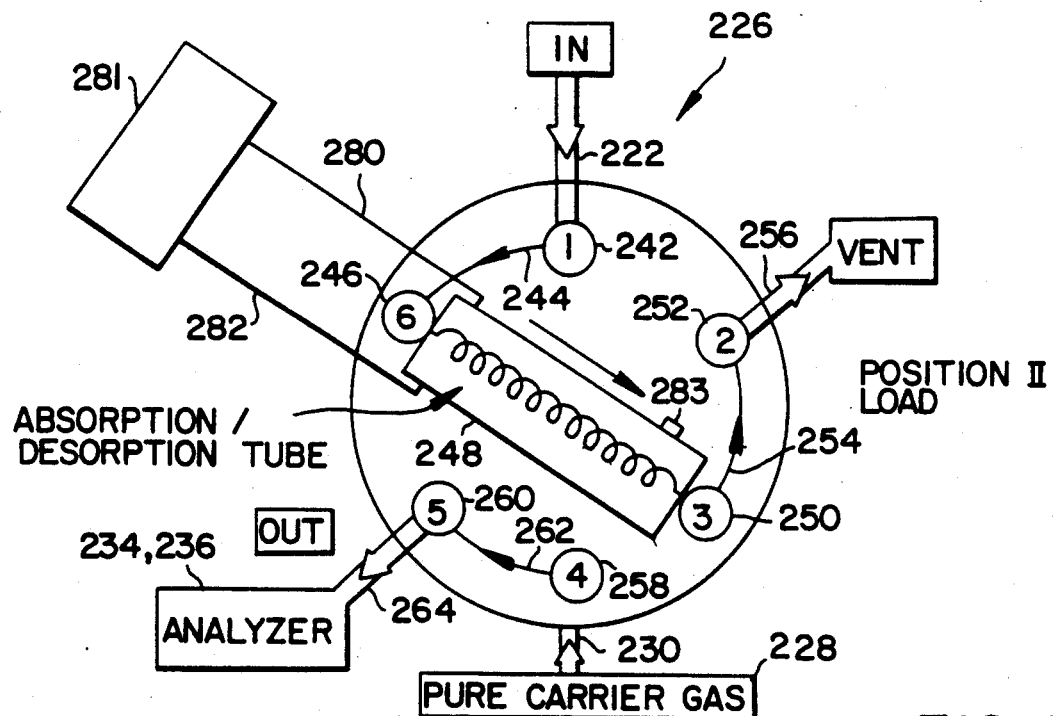
FIG. 10a is a diagrammatic representation of the multi-port valve used in the present invention with the valve in the load position.
Figure 10B:
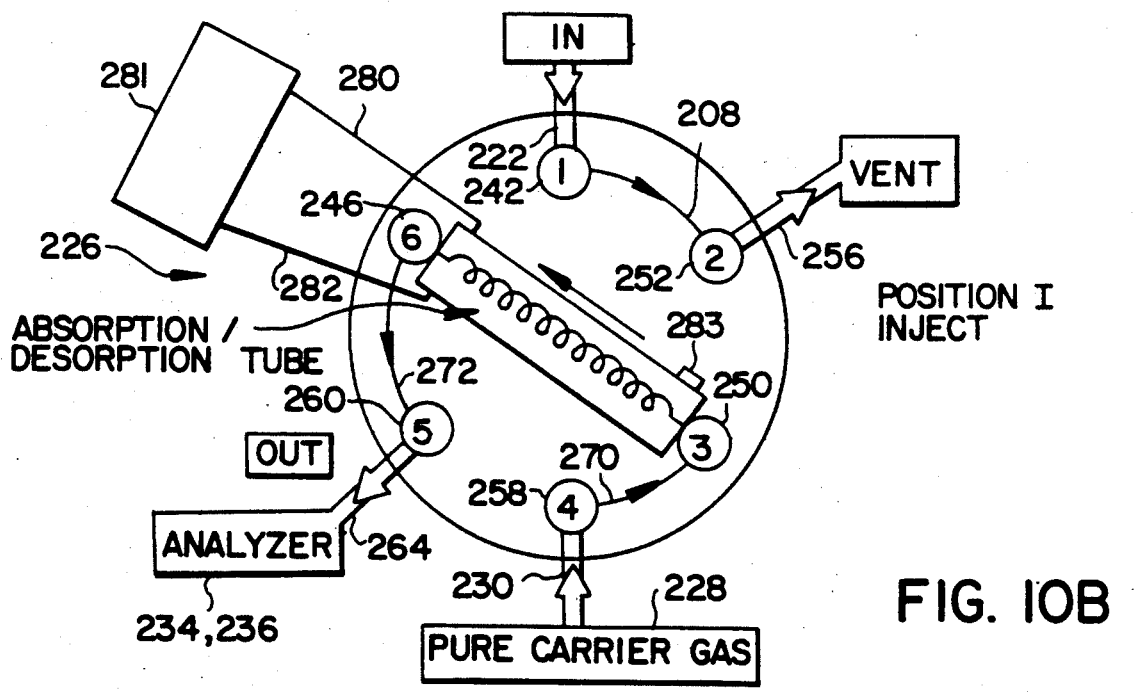
FIG. 10b is a diagrammatic representation of the multi-port valve used in the present invention with the valve in the inject position.

The multiport valve system 226 is a switching network with multiple ports as the name suggests. In one embodiment of the present invention, the multiport valve system 226 is a six-port valve. FIGS. 10A and 10B represent the two positions that the six-port valve 226 can occupy. The interface control unit 238, is a stepper motor, and is operable to switch the six-port valve 226 between the two positions. In either position, only pairs of ports are connected. In position 1, illustrated in FIG. 10B, ports 1 and 2, 3 and 4, and 5 and 6 are connected, and in position 2, illustrated in FIG. 10A, ports 2 and 3, 4 and 5, and 6 and 1 are connected. Position 2 places the adsorb-desorb tube 248 in the load position. The gas flow line 222 shown in FIG. 7 carries the gas containing the target material and some contaminants into port 1 indicated at 242 in FIG. 10A of valve 226 wherein the gas automatically flows through an internal passageway 244 to port 6, indicated at 246 in FIG. 10A. Connected between port 6 and port 3 is an external adsorption/desorption tube 248 in which the gas containing the target material and some minor contaminants pass through. The adsorbing material inside the tube 248 is specifically targeted for the target material; therefore, the carrier gas and the contaminants flow through the tube 248 to port 3, indicated at 250 while the target material is adsorbed within the tube. The carrier gas and contaminants flow from port 3 indicated at 250 in FIG. 10A to port 2 indicated at 252 in FIG. 10A through internal passageway 254, and is vented to the external atmosphere through exhaust line 256. Pure carrier gas supplied from gas supply 228 shown in FIG. 7 is fed into port 4 indicated at 258 via line 230. The pure carrier gas automatically flows from port 4 indicated at 258 to port 5 indicated at 260 via internal passageway 262. The carrier gas then flows from port 5, indicated at 260 to either of the chemical analyzers 234 or 236 via line 264. The analyzers 234, 236 require a continuous gas flow to remain operational. The use of multiport valve systems allows pure carrier to be fed gas continuously to the analyzers 234, 236, even when the adsorb/desorb tube 248 is in the adsorb cycle.

At the end of the adsorption cycle, the computer of the control system then automatically switches the six-port valve 226 into position 1 which is the desorb mode as shown in FIG. 10B. Port 1, indicated at 242 in FIG. 10B still receives gas from the primary concentrator 201 via line 230; however, the gas flows from port 1, indicated at 242 to port 2, indicated at 252 via internal passageway 268 and is vented to the atmosphere via exhaust line 256. Port 4, indicated at 258 is injected with pure carrier gas from supply 228 via line 230 which flows to port 3, indicated at 250 via internal passageway 270. As stated before, port 3, indicated at 250 and port 6, indicated at 246 are connected via an external adsorption/desorption tube 248; however, in this position, the carrier gas is flowing through the tube 248 in the opposite direction. Therefore, when the tube 248 is heated to desorption temperature, the gas will sweep the desorbed target material and carry it to port 6, indicated at 246 free of atmospheric contaminants. From port 6, indicated at 246, the target material flows to port 5, indicated at 260, via internal passageway 272 and to the chemical analyzers 234 and 236 via line 264.

The external adsorption/desorption tube 248 is electrically insulated from the valve body and contains a selected quantity of the adsorbing material which has the best characteristics for adsorbing the target material. High current connections are made to the ends of this tube 248 and are shown in FIGS. 10A and 10B as electric lines 280 and 282. Lines 280 and 282 are connected on the other end to a controlled current source 281. A thermocouple 283 is shown attached to tube 248 in FIGS. 10A and 10B. This thermocouple 283 as stated previously, is used to raise the temperature of the tube 248 so as to achieve the proper temperatures for desorption. The gas sample which contains the target material, contaminants and excess gas, passes through the tube 248 and because it is cold, and the adsorber material has been selected to be a strong adsorber for the target-material, most of the sample will be adsorbed at the end of the tube 248 near port 6. The contaminants are less strongly adsorbed and thus any adsorption of them will be throughout the length of the tube 248. Also, because the contaminants are not strongly adsorbed a larger portion of them will pass through the tube to the exhaust vent 256 and be discarded.

A desirable property of thermal desorption of gases or vapors on solid or liquid substrates is that the process can be highly thermally sensitive and thermally dependent. At a specified temperature the amount of any material desorbed is related to its physical and chemical properties and the physical and chemical properties of the adsorbing material. It is possible to choose adsorbing materials such that the contaminating materials are desorbed at a workable lower temperature than the target materials.

Careful thermal programming allows one to use these properties. An example is to heat the desorber tube 248 in a controlled fashion with the valve 226 in position 2. The contaminants such as water vapor etc. are not strongly adsorbed and a low temperature will cause a major portion of them to leave the adsorber and pass out of the system through the vent. At the same time, the target materials will not be desorbed and will remain at the end of the adsorber tube 248 adjacent port 6. If the position of the rotor in the six-port valve is now changed to the 1 position, two important changes are made. The adsorber tube is now connected to the next stage in the sequence and the pure carrier gas flows through the adsorber tube in the opposite direction to the previous gas flow direction. A rapid controlled increase in temperature will now cause the sample to be desorbed in a short period of time. This results in a sample which has been purified by the previously described adsorption and desorption process passing to the next stage in the process, contained in the minimum of pure carrier gas. Thus the sample has been twice purified of contaminants and concentrated in a much reduced volume of pure inert carrier gas.

The next step in the purification and concentration process may be another six-port valve with a smaller diameter desorption tube. The final desorption tube should match in diameter the size of the column in one of the analyzers, such as analyzers 234, which is a gas chromatograph. If this is done, it results in ideal sample injection into the gas chromatograph. In fact, it is possible by careful design and construction to have the desorber tube the same internal diameter as a capillary gas chromatograph column. It is possible to use the tube connecting two six-port valves as a desorber tube for purification and concentration purposes. It may be packed with adsorber and fitted with heating and temperature measuring equipment such as electrical connections and thermocouples.

The adsorbent material used in the various stages of concentration of the target materials may be selected from a group of materials commonly used for vapor sampling including Tenax and Carbotrap. There are other adsorbing materials that can be used with the present invention depending on the particular materials that are to be detected and isolated.

The SCAP 200 also contains an attachment for a portable sampling device 292 which is shown in FIG. 11A. The connection is a pipe 223 which is connected to pipe 118 shown in FIG. 7 or 8 through valve 221. The pipe 118 may be stainless steel, aluminum or even ABS plastic. Normally, fan 202 draws an air sample from the chamber 100; however, when valve 299 closes off the chamber 100 and valve 221 is opened, fan 202 will draw an air sample from the wand 292. The wand 292 is capable of drawing vapor and/or particulate emissions from a specific area on an individual or object. The wand 292 is used to sample an individual intensively when the results from the pass through the chamber 100 are inconclusive.

A second use for the hand held wand 292 would be to draw vapor and/or particulate emissions from baggage that is going to be stored in the cargo hold of the airplane. The system including the hand held wand 292 has proven very effective as a means of detecting explosive vapors in packages and baggage. In tests wherein the hand held wand 292 has been held against cardboard box packages and various types of luggage, positive identification of low levels of explosive vapors, equivalent to approximately a third of a stick of dynamite, are made. In addition, the hand held wand 292 can be attached to a sampling box 294 as shown in FIG. 11B that is placed over luggage to enhance the efficiency of detection and provides a means to automate baggage screening by including a conveyor belt 298. The wand 292 is attached to sampling box 294 through connection means 296.

Figure 12A:
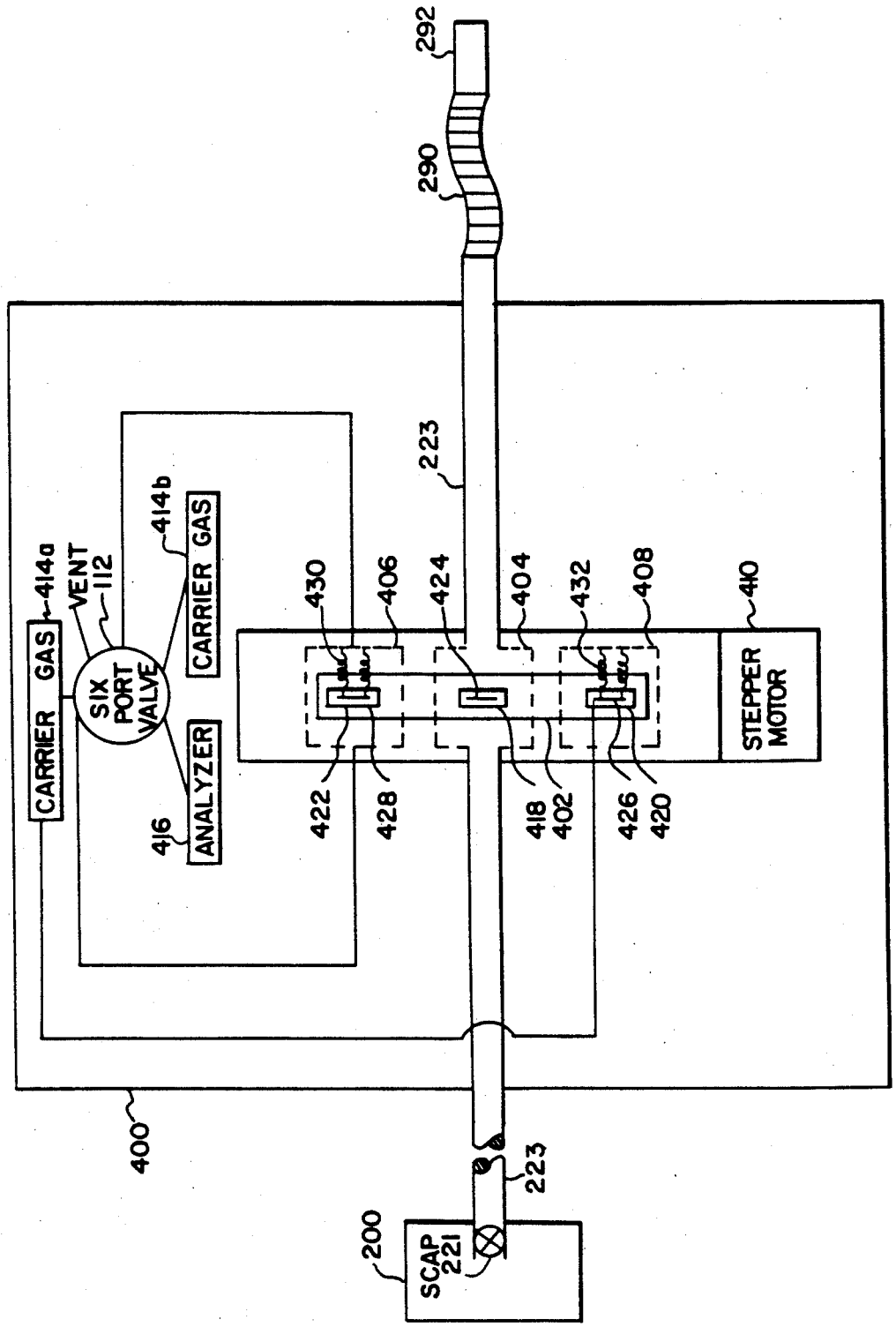
FIG. 12a is a diagrammatic representation of the particulate collector and detector means of the present invention utilizing a six-port valve configuration.

In a second embodiment for the portable sampling device 292, a particulate collector and detector (PCAD) 400 is incorporated. The PCAD 400 is located in line with stainless steel pipe 223 between valve 221 and flexible hose 290 as shown in FIG. 12a. The PCAD 400 consists of a rotating circular plane 402, a collection chamber 404, a desorption chamber 406, a flushing chamber 408, a stepper motor 410, a six-port valve 412, a pair of gas supplies 414a and 414b and a chemical analyzer 416. The rotating circular plane 402 has three circular holes 418, 420, and 422 equally spaced 120 degrees apart and covered with stainless steel mesh screens 424, 426 and 428. The rotating circular plane 402, which is actuated by the stepper motor 410, is rotated 120 degrees every sampling period so that each one of the holes 418, 420 and 422 occupies either the collection chamber 404, the desorption chamber 406 or the flushing chamber 408. To illustrate the operation of the PCAD 400, a complete 360 degree rotation of the circular plane 402 will be described.

For the purposes of this illustration, it is assumed that hole 418 with screen 424 is inside the collection chamber 404 at the start-up time. In this position, the hole 418 and screen 424 is directly in line with stainless steel pipe 223, and thus the screen 424 covering hole 418 is capable of collecting particulate matter that may be drawn from the hand held wand 292 during a sampling period. The particulate matter may be small particles or droplets of the target material itself or small particulates or droplets attached to dust particles or other vapor droplets. The particulate matter drawn in through wand 292 is physically trapped or adsorbed on screen 424. Any particulate matter not trapped on the screen 424 passes directly through to the SCAP 200 for standard preconcentration. The stainless steel screen can be varied in mesh size so as to be able to collect specific size particulates. Upon completion of the sampling period, stepper motor 410 is engaged by the control system (described subsequently) and rotates circular plane 120 degrees placing hole 418 and screen 424 inside the desorption chamber 406.

The desorption chamber 406 is a sealed chamber which contains a pair of electrical terminals 430 which connect to stainless steel screen 424 when that particular screen occupies the desorption chamber 406. The pair of terminals 430 provide a computer controlled current to the stainless steel screen 424 in order to generate a specific amount of heat energy to effectively desorb the collected particulate matter. After the desired temperature for desorption is reached, a small quantity of carrier gas from gas supply means 414a sweeps the desorbed material from the desorption chamber 406 via line 401 into the six-port valve 412. The operation of the six-port valve 412 is exactly the same as was described previously with an injection position and a load position. During the injection cycle, the further concentrated sample is injected into the chemical analyzer 416. In this embodiment, the analyzer 416 is a gas chromatograph. Note that during the desorption process wherein hole 418 and screen 424 are in the desorption chamber 406, hole 420 and screen 426 are inside the collection chamber 404 collecting the next sample of particulate matter. Upon completion of the desorption of the particulate matter, the stepper motor 410 is engaged and circular plane 402 is rotated 120 degrees placing hole 418 and screen 424 inside the flushing chamber 408, hole 420 and screen 426 inside the desorption chamber 406 and hole 422 and screen 428 in the collection chamber 404.

The flushing chamber 408 is a sealed chamber similar to desorption chamber 406. In this position, a second pair of electrical terminals 432 are connected to screen 424. The second pair of electrical terminals 432 provide a computer controlled current to generate a specific amount of heat energy to desorb any remaining particulate matter remaining on screen 424. A gas flow from gas supply 414a is used to sweep the desorbed material into the ambient environment through a vent in the chamber 408. Note that during the flushing process, hole 420 and screen 426 are inside the desorption chamber 406, and hole 422 and screen 428 are in the collection chamber 404 collecting the next sample of particulate matter.

Figure 12B:
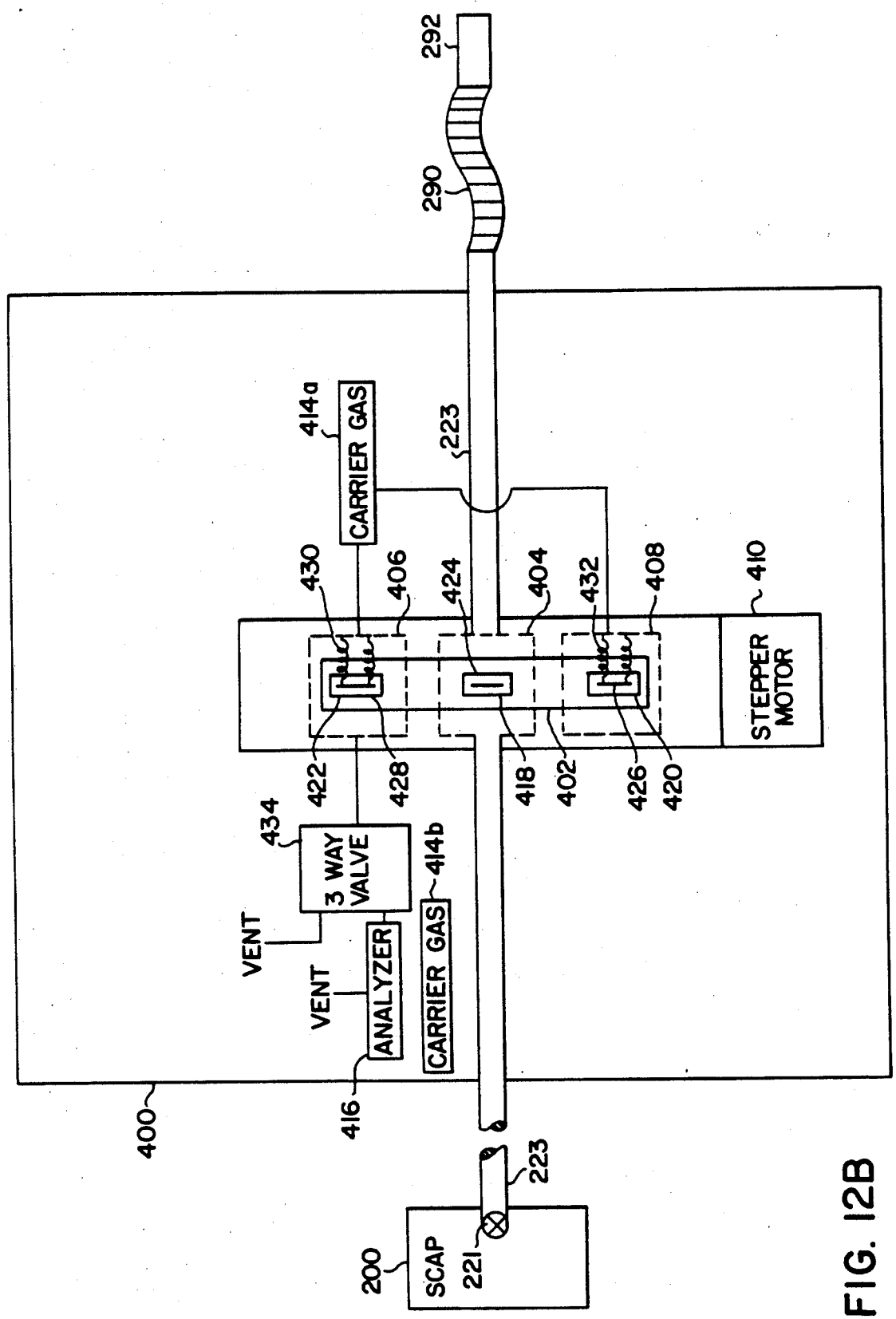
FIG. 12b is a diagrammatic representation of the particulate collector and detector means of the present invention utilizing a three-way valve configuration.

In an alternate embodiment for the PCAD 400, the analyzer 416 is a ion mobility spectrometer. The alternate embodiment is shown in FIG. 12b. As is shown in the figure, the only significant change is the substitution of a three-way valve 434 for the six-port valve 412. In this embodiment, the desorption process is identical to that previously described; however, the carrier gas sweeps the desorbed material into a three-way valve 434 instead of the six-port valve 412. The three-way valve 434 is a simple device which either vents the incoming flow of gas from gas supply 414a into the ambient environment or into the analyzer 416.

The PCAD 400 is designed in such a way that the movement of the circular plane 402 places holes 418, 420 and 422 in tightly sealed positions at each location so there is no contamination with the ambient air. The precise movement of the circular plane 402 is automatically controlled by the control system (to be described subsequently) and actuated by the stepper motor 410.

ANALYSIS

The analysis of the purified target material consists of identifying the materials and determining the amounts present. Because the original concentrations were so low with respect to many other common ambient materials it is possible for there to be, even under the best of purification and concentration systems, some remaining impurities of materials with similar characteristics to the target materials. Thus the analysis system must be capable of separating the target material response from the response due to interfering materials.

Two forms of analysis systems are used either separately or in combination. These systems are an ion mobility spectrometer (IMS) 236 based analysis system and a gas chromatograph (GC) 234 based system. The final detector for the GC 234 is usually a electron capture detector (ECD) but the IMS 236 can also be used as the detector if desired. Depending on the application, an photo ionization detector or a nitrogen-phosphorus detector or some other detector may be also used following this. The GC 234 may be of the "packed column" type or the capillary column type. Both analyzers 234 and 236 can be used separately or in a combined fashion. Valve 235 is used to direct the collected and purified sample to either or both of the analyzers. The analyzer 416 used in the PCAD 400 is either a gas chromatograph or ion mobility spectrometer and it exists as a separate entity from the analyzers of the SCAP 200, but its operation is identical to the above described analyzers.

Whatever analysis system is used the analysis must be completed in a time that is short enough that the free flow of people, luggage and baggage is not unduly inhibited. This also implies that the time for the concentration and purification process is short as well.

If all the valves in the system are motor driven or solenoid driven valves, the flow directions timings and magnitude may be controlled and varied. The time and temperature parameters are controlled and variable. Thus the physical characteristics of the complete system may be adjusted to detect a wide range of target materials and the sensitivities may be adjusted to accommodate a wide range of threats as perceived by the authorities using the system.

All the processes involved in the collection and concentration as well as the final analysis of the collected material is controlled by the computer of the control and data processing system and will by fully explained in the following section.

CONTROL AND DATA PROCESSING

The primary requirement for the control and data processing system of the screening system is that it reports the presence of, and if required, the level of specified substances. This means that the equipment must be configured and controlled to make the required measurement and it also means that the result must be presented to the user in a usable form. The subject or target materials may be present in varying amounts in the environment of the system and therefore, the system must be capable of distinguishing between this background level and an alarm level. It may also be a requirement to report on this background level.

A secondary requirement for the control and data processing system of the integrated system is self diagnostics, as there may be considerable time between alarms, the control and data processing system must be capable of performing confidence checks that are satisfactory to the operator on demand. There must also be routine self checks and calibration procedures performed on the total system by the control and data processing system. Basically, this ensures that the test results, whether positive or negative, must be believable.

A third requirement for the control and data processing system is ease of reconfiguration and versatility. The range of target materials may be changed from time to time, and the system must be capable of varying its internal operation parameters under program control to detect these materials. It is desirable that the rigor of the measurement in terms of time constraints and number and types of substances detected be alterable in an expeditious fashion at any time. The user's requirements in terms of level of threat and types of materials may quickly change and the equipment must respond to these changing needs.

The final requirement for the control and data processing system is that the parameters and operations of the sampling chamber and the SCAP must be monitored and controlled. This means that all internal timings, temperatures and mechanical components must be controllable by the control and data processing system.

The primary method of achieving these requirements is to put the total system under the control of a stored program digital computer. This computer through a series of modularized software routines performs the data analysis and presents the results in the required form to the user. The computer through another series of modularized software routines continuously performs self diagnostics and self calibration procedures on the total system, and alerts the user to any potential problems. The computer through still another set of modularized software routines controls all the processes of the total system and shall be more fully explained in subsequent paragraphs.

One primary benefit of this system of control is reliability. By themselves the components are rugged and reliable and not prone to failure. However, any system made up of many items is subject to drifts due to ambient changes and time. By having all components under program control and by arranging for a known input to the system such as a controlled injection of target material or target simulant, there can be a calibration and self-diagnostic program. The function of this program is to calibrate the entire system and determine and store the required time and temperature parameters, etc. If these parameters are not within specified limits for any reason, the program can alert the user. Guided by a service program the user response can range from immediate shutdown to scheduling service at a later date, to simply noting the circumstances. By use of a modem this information can be easily transmitted to anywhere in the world. The other aspect of reliability in a system of this type is that the user must know that the system is reliable. Hopefully there will be very long periods of time between actual alarm events. However, if there is a calibration and self diagnostic program and associated hardware for realistic sample injection, the user can generate, at anytime, an actual/simulated alarm event as a confidence check.

The second primary benefit of this system of control is versatility. It is advantageous for the system to have the capability of detecting a wide range of explosives, a range of controlled chemical agents, drugs, and narcotics etc. All these materials have differing physical and chemical properties. These properties give rise to a set of internal parameters for optimum detection. However these parameters will be less than optimum for some other materials. But, if these parameters are all controllable and easily changed such as by simply reading in or activating a different program in the computer memory, then the user can effectively change the system to meet what is considered to be the threat at that time without making any hardware changes.

Referring now to FIG. 13, there is shown a block diagram representation of the control and data processing system 300 and its associated peripheral elements. The digital computer 302 or processor is an AT type personal computer running at 10 MHz and has a standard video display terminal 304. The computer 302 is responsible for process control, data acquisition, data analysis and display of results. In addition, as mentioned previously, the computer 302 also contains software routines for self diagnostics and self calibration procedures. The computer 302 receives power from the power distribution unit 306 as does the sampling chamber 100, the hydraulic pump 210b which supplies hydraulic pressure for the hydraulic control unit 210a, and the process control unit 308. The process and control unit 308 under the control of the computer 302 interfaces and provides the necessary signals to run the hydraulic control unit 210a, the preconcentrator control unit 214 and the interface control unit 238.

The process and control unit 308 is a standard interface unit between computer 302 and the various actuators. The hydraulic actuator unit 210a determines the drive direction of the hydraulic piston which travels up and down to unlock and lock the filter elements 206 and 208 of the primary preconcentrator 201, as shown in FIG. 7, so they can be rotated from position 1 to position 2 as described in the previous section. Under software control, the process control unit 308 outputs commands to the hydraulic actuator unit 210a which is a two-way solenoid, not shown, and engages or disengages the hydraulic piston. The preconcentrator actuator unit 214 is a stepper motor which rotates the filter elements 206 and 208 after they are no longer locked in place by the hydraulic actuator unit 210a. The stepper motor is run under software control. The interface actuator unit 238 is also a stepper motor, and it is used to rotate the multi-port valve 226, used in the secondary preconcentrator 203, from position 1 to position 2 and vice versa. The PCAD actuator unit comprises two stepper motors, one for the rotation of the circular plane 402, and one for the actuation of the six-port valve 412 or the three-way valve 434. Data from the analyzers 234 and 236 is brought directly into the computer 302 for processing. Data from the gas chromatograph/ECD system 234 is taken into the computer 302 as a varying frequency, and data from the IMS system 236 is taken into the computer 302 as a varying analog voltage. The data input to the computer 302 is correlated by processor 302 to the process control module 308 which generates the necessary interrupts for processor 302 so the data can be input at the proper time intervals.

The computer 302 has an internal clock which provides the reference clock for all timing sequences. Therefore, because all the valves and mechanical motions are being actuated by the computer, all gas and sample flows in the equipment are controllable with respect to the time of actuation. The relative sequencing and timing of actuations are simply steps in a stored program in the memory of the computer. In addition, all the temperatures in the equipment are read into the computer and all heating functions are actuated by the computer. Therefore, all the temperatures and their magnitudes at any time and rate of change with respect to time are under program control. The data output from the ECD 234 and the IMS 236 are processed as necessary and the required information is extracted and displayed by the same computer.

Figure 14A:
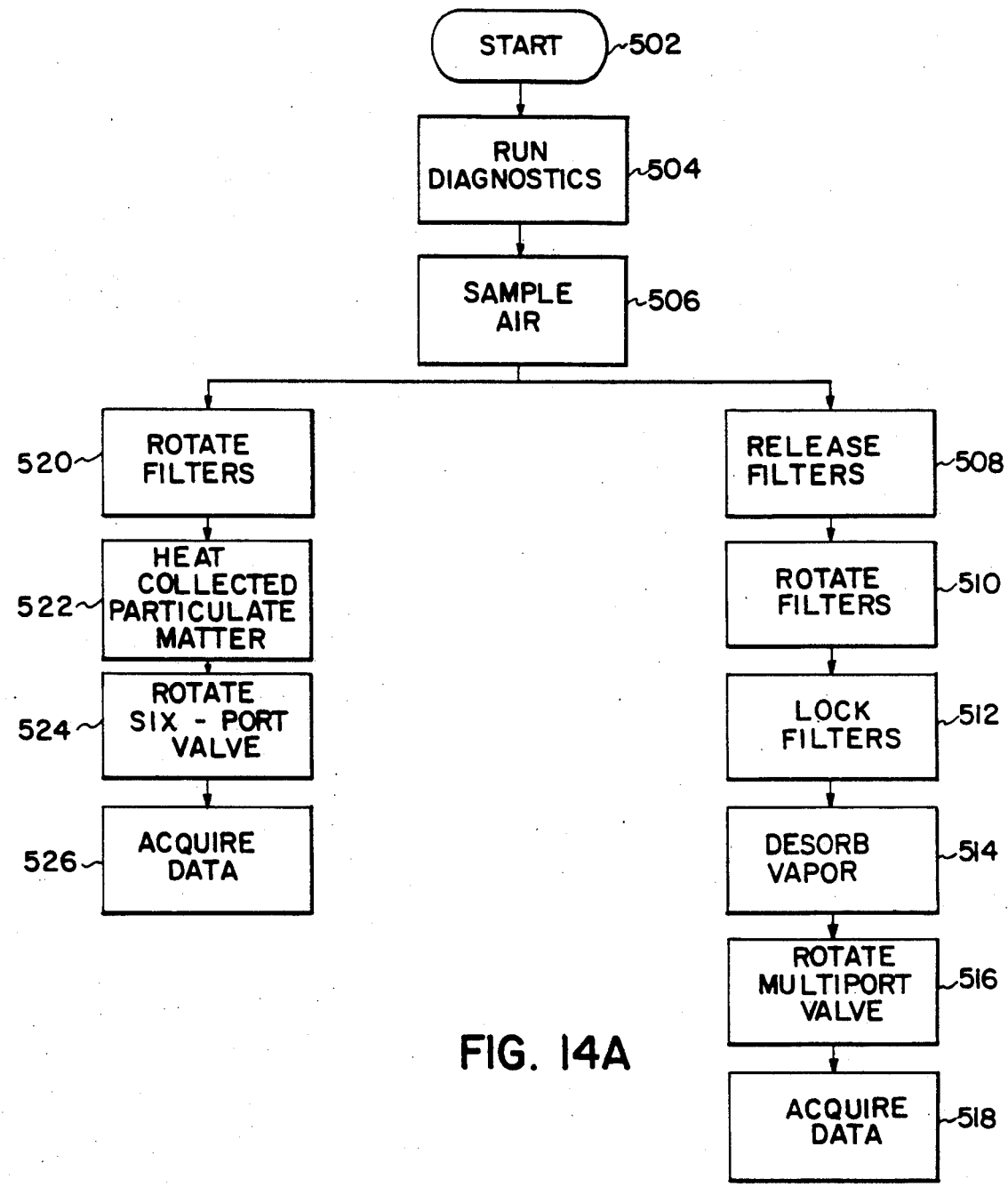
FIG. 14a is a flow chart of the computer program used in the present invention utilizing a six-port valve configuration for the particulate collector and detector means.

FIG. 14a is a flow chart 500 showing the overall process control as accomplished by the control and data processing systems and run by the computer 302. Block 502 of flow chart 500 is simply the starting point or entry into the entire software package. The Run Diagnostics block 504 represents the block of software that is responsible for self diagnostics and self calibration. The Sample Air block 506 represents the block of code that causes the air sample drawn from the sampling port of the sampling chamber to be drawn into the SCAP. After the Sample Air Block 506, the flow chart 500 diverges into two paths that can run simultaneously. One path represents normal SCAP 200 operation while the second path represents PCAD 400 operation. The first path is as follows: The Release Filters block 508 represents the block of software that is responsible for the control of the hydraulic control unit. The Rotate Filters block 510 represents the block of software responsible for the control of the preconcentrator control unit. The Lock Filters block 512 represents the block of software that is responsible for the control of the hydraulic control unit in that it commands the unit to lock the filter elements in the holding means. The Desorb Vapor block 514 represents the block of software that is responsible for the controlling of the heating means and the flow of pure gas in the desorption process. The Rotate Multiport Valve block 516 represents the block of software that is responsible for controlling the multiport valve of the secondary preconcentrator so that the concentrated sample is properly routed to the analyzers. The Acquire Data block 518 represents the block of software that is responsible for the acquisition of data from the analyzers and the subsequent analysis and display of the resultant data. The software is a cyclic process and following step 518, returns to sampling step 506 and continues until stopped. The second path is as follows: The PCAD Rotate Filters block 520 represents the block of software responsible for the control of the rotation of the circular plane. The PCAD Heat Collected Particulate Matter block 522 represents the block of software responsible for the electrical heating of the stainless steel screens during the desorption process. The PCAD Rotate Six-Port Valve block 524 represents the block of software responsible for controlling the six-port valve so that the concentrated sample is properly routed to the analyzer. The PCAD Acquire Data block 526 represents the block of software that is responsible for the acquisition of data from the analyzers and the subsequent analysis and display of the resultant data. The software is a cyclic process and following the step of block 526, returns to sampling step 506 and continues until stopped. As stated previously, the software routine is modularized and therefore can be easily changed, updated, removed or added on to.

Figure 14B:
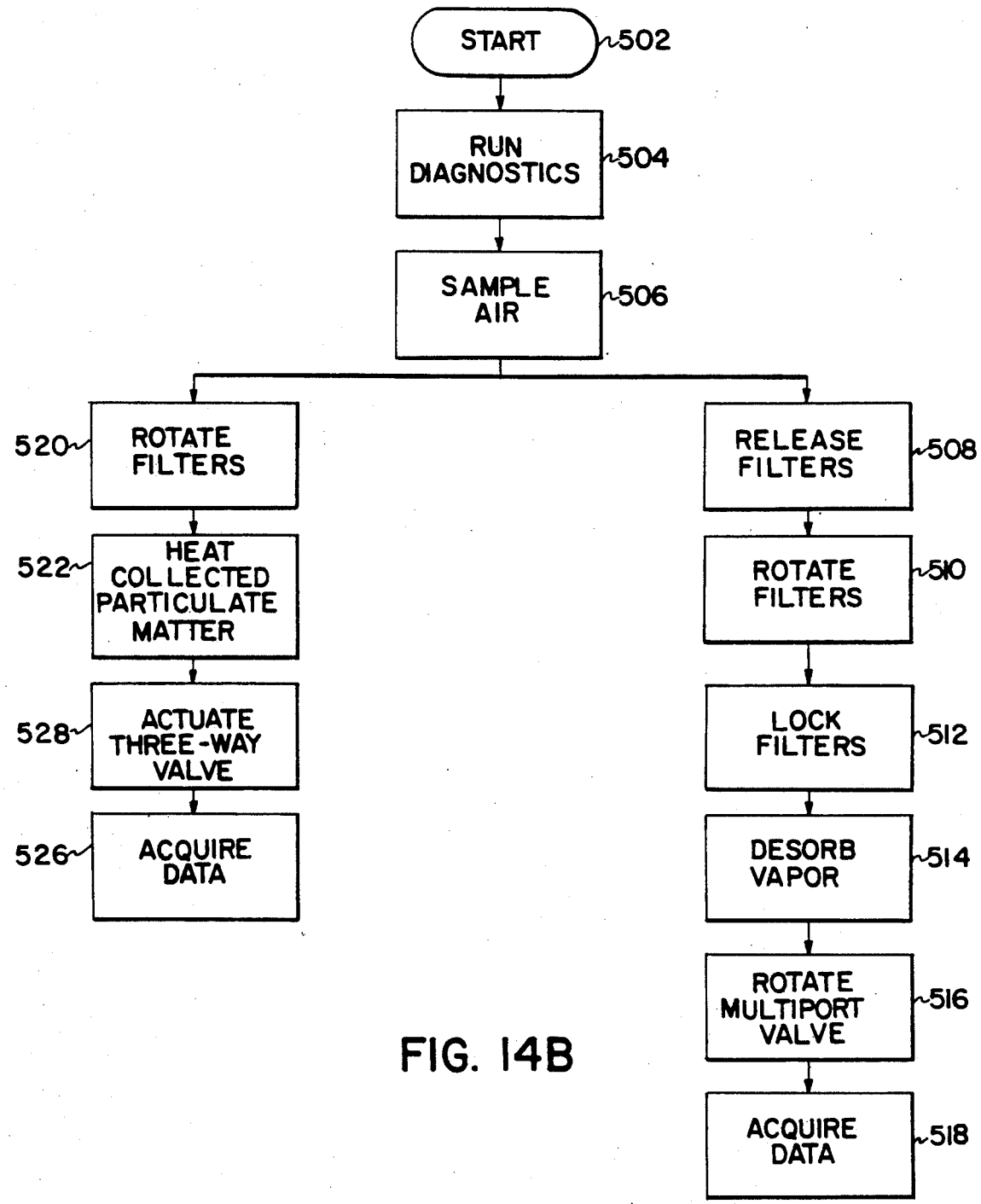
FIG. 14b is a flow chart of the computer program used in the present invention utilizing a three-way valve configuration for the particulate collector and detector means.

FIG. 14b is a flow chart 500' which shows an identical process as does the flow chart 500 in FIG. 14a with one exception. In flow chart 500', the PCAD Rotate Six-Port valve block 524 of FIG. 14a is replaced by a PCAD Actuate Three-Way Valve block 528. The PCAD Actuate Three-Way Valve block 528 represents the block of software responsible for controlling the three-way valve in the ion mobility embodiment so that the concentrated sample is properly routed to the analyzer.

There are two schemes that exist for the screening process. The sequential scheme requires approximately 14.0 seconds to complete one screening cycle and the concurrent scheme requires approximately 3.6 seconds to complete one screening cycle. Both schemes are implemented using flow charts 500 and 500' illustrated in FIGS. 14a and 14b; however, as the name implies, the concurrent scheme involves performing certain of the operations involved in the screening process in an overlapping or multi-tasking environment. Basically, in the concurrent scheme, the software routines are run in a foreground/background scenario in a true interrupt mode. In this type of scenario the mechanical operations can be run in background while the analysis and data processing can be run in foreground. FIGS. 14a and 14b are a general representation of the software and should not be construed as a timing diagram. Table 1 given below illustrates the required steps and associated times involved in the screening procedure utilizing the sequential scheme.

TABLE 1

| | |
|---|---|
| SAMPLE COLLECTION | 5.0 seconds |
| PRIMARY CONCENTRATION STAGE | 3.0 seconds |
| SECONDARY CONCENTRATION STAGE | 2.0 seconds |
| ANALYSIS | 3.0 seconds |
| DATA PROCESSING/REPORTING | 1.0 seconds |
| TOTAL SCREENING TIME | 14.0 seconds |

Referring now to FIG. 15, a sequence diagram 600 or timing chart is given in order to illustrate the various time parameters for each given in the concurrent sampling scheme. Each time bar is comprised of five boxes indicating the various steps in the process. Box 602 represents the air sampling step time, box 604 represents the time for the mechanical steps involved in the collection of the sample, box 606 represents the time associated for injecting the concentrated sample into the chemical analyzers, and box 610 represents the analysis time. Since it takes approximately 2.5 seconds to pass through the portal, two people can pass through in 5.0 seconds, and thus the timing chart 600 is shown for two people. To calculate the total time for a single person, which is approximately 3.6 seconds, the total time for the first two people to be screened, which is 14.4 seconds, has subtracted from it the time for sampling and collecting the sample from the next two people, which is approximately 7.2 seconds, resulting in a time of approximately 7.2 seconds for two people and 3.6 seconds for a single person. As indicated in chart 600, the concurrent scheme overlaps in the sampling and collection periods. The three remaining time lines are identical numerals with prime, double prime and triple prime added.

Although shown and described in what is believed to be the most practical and preferred embodiments, it is apparent that departures from specific methods and designs described and shown will suggest themselves to those skilled in the art and may be used without departing from the spirit and scope of the invention. The present invention is not restricted to the particular constructions described and illustrated, but should be constructed to cohere of all modifications that may fall within the scope of the appended claims.

What is claimed:

1. A walk-through explosive detection screening system for the detection of concealed explosives, chemical agents and other controlled substances such as drugs or narcotics by detecting their vapor or particulate emissions, said system comprising:
   (a) a walk-through sampling chamber means for gathering a sample of the environment surrounding a person or object passing through said sampling chamber means by sweeping the vapor or particulate emissions from said person or object, said sampling chamber means having an entrance and exit portal defined by at least two walls, and a convergent ceiling which opens into an air plenum;
   (b) a pair of inwardly directed and vertically oriented air flow guide means on either side of each of said entrance and exit portals, said air flow guide means directing air towards a center region of said sampling chamber means with a predetermined velocity, the combination of said air flows from said pair of inwardly directed and vertically oriented air flow guide means creating a dynamic high pressure zone in said sampling chamber means;
   (c) means for recirculating air between said pair of inwardly directed and vertically oriented guide means and said air plenum, the recirculating air creating a dynamic low pressure zone in the region of said convergent ceiling, said dynamic high and low pressure zones creating a region within said sampling chamber means that does not allow an appreciable amount of air in or out of said entrance and exit portals;
   (d) a sample collection means to collect a sample volume of air that is swept off the individual or object passing through said sampling chamber means, said sample collection means including means for collecting a volume of air from a sampling port mounted in the plenum and centered in said convergent ceiling;
   (e) means for concentrating said vapor or particulate emissions collected by said sample collection means, said means for concentrating having a first means for adsorption and a second means for desorption of said concentrated vapor or particulates;
   (f) detecting means responsive to said vapor or particulate emissions desorbed from said second means for desorption to generate a first signal and an alarm.

2. The walk-through explosive detection screening system of claim 1 wherein said walk-through sampling chamber means has a rectangular geometry approximately six feet in length, three feet in width and seven feet in height, said walk-through sampling chamber means having a conically shaped ceiling.

3. The walk-through explosive detection screening system of claim 2 wherein said pair of inwardly directed and vertically oriented air flow guide means are six slots of one foot in length and a half inch in width in a pair of six inch diameter end columns mounted on either side of each of said entrance and exit portals, said end columns having inch and a half internal guide vanes to form exiting air into a first jet stream.

4. The walk-through explosive detection screening system of claim 3 wherein said six slots are at an angle of 45 degrees pointing towards the center of said walk-through sampling chamber means.

5. The walk-through explosive detection screening system of claim 3 wherein said first jet stream has a velocity of approximately 17 meters per second.

6. The walk-through explosive detection screening system of claim 5 wherein said walk-through sampling chamber means further comprises a pair of side air flow pipes, said pair of side air flow pipes run along said floor and are connected to each of said pair of six inch diameter end columns.

7. The walk-through explosive detection screening system of claim 6 wherein said pair of side air flow pipes each contain a twelve inch long by half inch wide air slot in the center of each of said pair of side air flow pipes, said air slots forming exiting air into a second jet stream.

8. The walk-through explosive detection screening system of claim 7 wherein said air slots are at an angle of 45 degrees pointing upwards to the center of said walk-through sampling chamber means.

9. The walk-through explosive detection screening system of claim 8 wherein said second jet stream has a velocity of approximately 15 meters per second.

10. The walk-through explosive detection screening system of claim 7 wherein said means for recirculating air comprises a plurality of fans connected on a suction end to said plenum and on a discharge end to said pair of six inch diameter end columns.

11. The walk-through explosive detection screening system of claim 10 wherein said plurality of fans are each capable of delivering 1000 cubic feet of air per minute.

12. The walk-through explosive detection screening system of claim 1 wherein said sampling port is centered in a collection duct having a rectangular geometry with dimensions of 16 inches by 20 inches by 6 inches.

13. The walk-through explosive detection screening system of claim 11 wherein said sample collection means further includes a transportation means for collecting said volume of air from said sampling port and transporting said volume of air to said concentrating means.

14. The walk-through explosive detecting screening system of claim 13 wherein sample collection means further comprises:
   portable sampling device to collect a sample volume of air from a specific area;
   a particulate collector and detector means for collecting and concentrating particulate emissions collected by said portable sampling device.

15. The walk-through explosive detecting screening system of claim 14 wherein sample collection means further comprises a sampling box for collecting a sample volume of air that is drawn off luggage that is placed in said sampling box, said portable sampling device is connected to said sampling box for drawing said sample volume of air.

16. The walk-through explosive detection screening system of claim 13 wherein said transportation means is a pipe with a first end open as said sampling port and a second end connected to a suction fan for drawing said volume of air from said sampling port at predetermined times, said pipe can be stainless steel, aluminum or ABS plastic.

17. The walk-through explosive detection screening system of claim 16 wherein said concentrating means comprises a primary preconcentrator.

18. The walk-through explosive detection screening system of claim 17 wherein said first means for adsorption and said second means for desorption are first and second filter means mounted on a movable platform.

19. The walk-through explosive detection screening system of claim 18 wherein said first and second filter means are movable between an adsorption position and a desorption position, each of said filter means being in line with said suction fan and operable to adsorb vapor and/or particulate emissions contained in said volume of air in said adsorption position, and each of said filter means being in line with an interface means when said adsorbed vapor and/or particulate emissions are desorbed.

20. The walk-through explosive detection screening system of claim 19 wherein said primary preconcentrator further comprises a third filter means mounted on said movable platform between said first and second filter means.

21. The walk-through explosive detection screening system of claim 20 wherein said first, second and third filter means are movable between said adsorption position, said desorption position, and a thermal cleaning position, each of said filter means being in line with said suction fan and operable to adsorb vapor and/or particulate emissions contained in said volume of air in said adsorption position, each of said filter means being in line with an interface means when said adsorbed vapor and/or particulate emissions are desorbed, and each of said filter means being in line with a thermal cleaning means when other filter means are being adsorbed and desorbed.

22. The walk-through explosive detection screening system of claim 21 wherein said primary preconcentrator comprises a gas supply means for supplying a clean gas flow to said first, second and third filter means when said respective filter means is in said desorption position, and in said thermal cleaning position said clean gas flow is used to desorb and sweep said concentrated vapor and/or vapor emanating from particulate matter into said interface means when said filter means is in said desorption position, and said clean gas flow is used to thermally clean and sweep residue into the ambient environment.

23. The walk-through explosive detection screening system of claim 22 wherein said clean gas is an inert gas.

24. The walk-through explosive detection screening system of claim 23 wherein said first, second and third filter means comprise wire screens which hold a selected adsorbing material coated thereon.

25. The walk-through explosive detection screening system of claim 24 wherein said selected adsorbing material is targeted for collecting explosive compound vapors or particulates.

26. The walk-though explosive detection screening system of claim 24 wherein said selected adsorbing material selectively absorbs narcotic compound vapors or particulates.

27. The walk-through explosive detection screening system of claim 24 wherein said primary preconcentrator still further comprises a heat exchanger for supplying heat to each of said filter means when they are in said desorption and said thermal cleaning position to aid in desorbing the vapor and/or particulate emissions.

28. The walk-through explosive detection screening system of claim 22 wherein both said first, second and third filtering means are each movable between said adsorption position, said desorption position, and said thermal cleaning position, said second filter means occupying said desorption position when said first filter means occupying said adsorption position and when said third filter means occupying said thermal cleaning position, and said third filter means occupies said adsorption position when said first filter means occupies said desorption position and said second filter means occupying said thermal cleaning position.

29. The walk-through explosive detection screening system of claim 22 wherein said first, second and third filter means are moved by a control system.

30. The walk-through explosive detection screening system of claim 29 wherein said control system comprises:
 a hydraulic control unit and pump connected to said platform by a rigid shaft, said hydraulic control unit is operable to move said platform from a locked position to an unlocked position; and
 a preconcentrator control unit which is operable to rotate said platform when said platform is in the unlocked position.

31. The walk-through explosive detection screening system of claim 30 wherein said preconcentrator control unit is a stepper motor.

32. The walk-through explosive detection screening system of claim 14 wherein said portable sampling device is a hand held wand which is valve connected to said transportation means by a flexible pipe.

33. The walk-through explosive detection screening system of claim 14 wherein said particulate collector and detector means comprises:
 a rotating plate, said rotating plate defining an axis of rotation and having at least two openings, said two openings being circumferentially spaced about said axis of rotation and supporting stainless steel mesh screens for collecting particulate emissions from said portable sampling device;
 a collection chamber in line with said transportation means for receiving said rotating plate, said stainless steel mesh screens being exposed to and adsorbing emissions collected by said portable sampling device; and
 a desorption chamber for receiving said rotating plate, said stainless steel mesh screens being heated to desorb said collected emissions, whereby said desorbed emissions are swept into a valve means.

34. The walk-through explosive detection screening system of claim 33 wherein said particulate collector and detector means further comprises a PCAD actuator unit means for rotating said rotating plate a predetermined distance every sampling period and simultaneously controlling said valve means.

35. The walk-through explosive detection screening system of claim 34 wherein said desorption chamber comprises a first pair of electrodes which connect to said stainless steel mesh screens and apply a current to said screens to rapidly heat said screens and desorb the collected emissions.

36. The walk-through explosive detection screening system of claim 34 wherein said particulate collector and detector means further comprises a chemical analyzer means.

37. The walk-through explosive detection screening system of claim 36 wherein said valve means is a six-port valve, said six-port valve being an interface between said desorption chamber and said chemical analyzer means.

38. The walk-through explosive detection screening system of claim 36 wherein said valve means is a three-way valve, said three-way valve is an interface between said desorption chamber and said chemical analyzer.

39. The walk-through explosive detection screening system of claim 34 wherein said PCAD actuator unit means comprises first and second stepper motors.

40. The walk-through explosive detection screening system of claim 36 wherein said chemical analyzer is a gas chromatograph.

41. The walk-through explosive detection system of claim 36 wherein said chemical analyzer is an ion mobility spectrometer.

42. The walk-through explosive detection screening system of claim 14 wherein said particulate collector and detector means comprises:

- a rotating plate, said rotating plate defining an axis of rotation and having three openings, said three openings being circumferentially spaced about said axis of rotation and supporting stainless steel mesh screens for collecting particulate emissions from said portable sampling device;
- a collection chamber in line with said transportation means for receiving said rotating plate, said stainless steel mesh screens being exposed to and adsorbs emissions collected by said portable sampling device;
- a desorption chamber for receiving said rotating plate, said stainless steel mesh screens being heated to desorb said collected emissions, whereby said desorbed emissions are swept into a valve means; and
- a flushing chamber for receiving said rotating plate, said stainless steel mesh screens are heated to desorb any remaining collected emissions, said desorbed emissions are vented to the ambient environment.

43. The walk-through explosive detection screening system of claim 42 wherein said particulate collector and detector means further comprises a PCAD actuator unit means for rotating said rotating plate a predetermined distance every sampling and simultaneously controlling said valve means.

44. The walk-through explosive detection screening system of claim 34 wherein said desorption chamber comprises a first pair of electrodes which connect to said stainless steel mesh screens and apply a current to said screens to rapidly heat said screen and desorb the collected emissions.

45. The walk-through explosive detection screening system of claim 42 wherein said flushing chamber comprises a second pair of electrodes which connect to said stainless steel mesh screens and supply a current to said screen to rapidly heat said screen and further desorb the collected emissions.

46. The walk-through explosive detection screening system of claim 22 wherein said interface means is a connector tube which connects said primary preconcentrator to said detection means and which carries said concentrated vapor and/or vapors emanating from particulate matter from said primary preconcentrator to said detection means.

47. The walk-through explosive detection screening system of claim 22 wherein said interface means is a secondary preconcentrator which comprises a multiport valve system.

48. The walk-through explosive detection screening system of claim 47 wherein said multi-port valve system comprises a six-port valve which contains an adsorption/desorption tube connected across two of said six-ports and four gas lines, said six-port valve being rotatable between an adsorb position and an desorb position.

49. The walk-through explosive detection screening system of claim 48 wherein said six-port valve is rotated by an electronic interface control unit.

50. The walk-through explosive detection screening system of claim 49 wherein said interface control unit includes a stepper motor.

51. The walk-through explosive detection screening system of claim 48 wherein the six-port valve is in said adsorb position when said concentrated vapor and/or vapor emanating from particulate matter is passed through said adsorption tube for further concentration.

52. The walk-through explosive detection screening system of claim 48 wherein the six-port valve is in said desorb position when said further concentrated vapor and/or vapor emanating from particulate matter is desorbed and swept into said detection means.

53. The walk-through explosive detection screening system of claim 48 wherein said adsorption/desorption tube further includes a thermocouple or thermistor for monitoring the desorption temperature of the tube.

54. The walk-through explosive detection screening system of claim 48 wherein said adsorption/desorption tube is electrically connected to a controlled current source which is used to heat the tube to a predetermined temperature as part of the desorption process.

55. The walk-through explosive detection screening system of claim 52 wherein said interface means further comprises a gas supply means for sweeping said further concentrated vapor and/or vapors emanating from particulate matter into said detection means.

56. The walk-through explosive detection screening system of claim 55 wherein said detection means comprises an ion mobility spectrometer (IMS) for analyzing said further concentrated vapor and/or vapors emanating from particulate matter and generating said first signal if a target material is detected.

57. The walk-through explosive detection screening system of claim 55 wherein said detection means comprises a gas chromatograph/electron capture detector for analyzing said further concentrated vapor and/or vapors emanating from particulate matter and generating said first signal if a target material is detected.

58. The walk-through explosive detection screening system of claim 55 wherein said detection means comprises a photo ionization detector.

59. The walk-through explosive detection screening system of claim 55 wherein said detection means comprises a nitrogen phosphorous detector.

60. The walk-through explosive detection screening system of claim 55 wherein said detecting means comprises an ion mobility spectrometer and a gas chromatograph/electron capture detector for analyzing said further concentrated vapor and/or vapor emanating from particulate matter and generating said signal if a target material is detected.

61. The walk-through explosive detection screening system of claim 60 wherein said system further includes a control and data processing means which further comprises:

- a digital computer with a stored digital program which is responsible for the control of the system; and
- a process control module which is an interface between said digital computer and said interface control unit, said preconcentrator control unit and said control unit.

62. The walk-through explosive detection screening system of claim 61 wherein said stored digital program is operable to control a plurality of processes including said self diagnostic and self calibration processes, control of said sample collection, and processing of collected data from said detection means.

63. A method for the detection of concealed explosive chemical agents and other controlled substances such as drugs or narcotics by detecting their vapor or particulate emissions, said method comprising the steps of:

(a) gathering a sample of the environment surrounding a person or object passing through a sampling chamber by sweeping the vapor or particulate emissions from said person or object;

(b) directing air towards a center region of said sampling chamber means with a predetermined velocity from a pair of inwardly directed and vertically oriented air flow guide means in order to create a dynamic high pressure zone in said sampling chamber, said dynamic high pressure zone creating a region within said sampling chamber that does not allow an appreciable amount of air in or out of an entrance and exit portal of said sampling chamber means;

(c) recirculating air between said pair of inwardly directed and vertically oriented guide means and an air plenum, the recirculating air creating a dynamic low pressure zone in the region of a convergent ceiling in said sampling chamber means;

(d) collecting a sample volume of air that is swept off the individual or object passing through a said sampling chamber means, said sample collection means including means for collecting a volume of air from a sampling port mounted in the plenum and centrally located in said convergent ceiling;

(e) concentrating said vapor or particulate emissions collected by said sample collection means, said means for concentrating having a first means for adsorption and a second means for desorption of said concentrated vapor or vapors emanating from particulate emissions;

(f) detecting said vapor or particulate emissions desorbed from said second means for desorption.

64. The method for the detection of concealed explosives according to claim 63 wherein said directing air includes forming exiting air into a first jet stream at an angle of 45 degrees pointing towards the center of said sampling chamber means with a velocity of approximately 17 meters per second.

65. The method for the detection of concealed explosives according to claim 64 wherein said directing air step further includes forming air exiting from a pair of side air flow pipes into a second jet stream at an angle of 45 degrees pointing upwards towards the center of said sampling chamber means with a velocity of approximately 15 meters per second.

66. The method for the detection of concealed explosives according to claim 65 wherein said collecting step further comprises transporting said volume of air to said concentrating means.

67. The method for the detection of concealed explosives according to claim 66 wherein said concentrating step comprises adsorbing target materials in a first position and desorbing target materials in a second position.

68. The method for the detection of concealed explosives according to claim 66 wherein said desorbing target materials in a second position comprises the steps of:

heating said target materials to a predetermined desorbing temperature or a predetermined vaporizing temperature; and sweeping said target materials with an inert gas.

69. The method for the detection of concealed explosives according to claim 67 wherein said step of detecting includes sweeping said target materials and inert gas into a detection means.

70. The method for the detection of concealed explosives according to claim 68 wherein said step of detecting further includes chemically analyzing said target materials.

71. The method for the detection of concealed explosives according to claim 70 which further includes the step of controlling the collection and processing of data with a digital computer which utilizes a stored program.

72. The method for the detection of concealed explosives according to claim 66 wherein said concentrating step further comprises thermally cleaning the residue from a third means for adsorption and desorption when said third means is in a thermally cleaning position.

73. The method for the detection of concealed explosives according to claim 72 wherein said thermal cleaning comprises the steps of:

heating said residue on said third means to a predetermined temperature; and sweeping said heated residue to the ambient environment.

* * * * *